US006860148B2

(12) United States Patent
Kossuth et al.

(10) Patent No.: US 6,860,148 B2
(45) Date of Patent: Mar. 1, 2005

(54) HIGH THROUGHPUT FABRIC HANDLE SCREENING

(75) Inventors: Mary Beth Kossuth, San Jose, CA (US); Damian A. Hajduk, San Jose, CA (US); Paul Mansky, San Francisco, CA (US)

(73) Assignee: Symyx Technologies, Inc., Santa Clara, CA (US)

(*) Notice: Subject to any disclaimer, the term of this patent is extended or adjusted under 35 U.S.C. 154(b) by 48 days.

(21) Appl. No.: 09/939,139

(22) Filed: Aug. 24, 2001

(65) Prior Publication Data

US 2003/0041663 A1 Mar. 6, 2003

(51) Int. Cl.⁷ .............................................. G01L 5/04
(52) U.S. Cl. ............................ 73/159; 73/788; 73/790; 73/794; 73/819; 73/849; 73/856
(58) Field of Search ........................ 73/159, 781, 788, 73/790, 794, 819, 849, 856; D15/122–143

(56) References Cited

U.S. PATENT DOCUMENTS

| | | | |
|---|---|---|---|
| 1,870,412 A | | 8/1932 | Kennedy |
| 2,590,839 A | * | 4/1952 | Claphan ........................ 73/7 |
| 2,786,352 A | * | 3/1957 | Sobota ........................ 73/159 |
| 3,071,961 A | | 1/1963 | Heigl et al. |
| 3,151,483 A | * | 10/1964 | Plummer ...................... 73/159 |
| 3,613,445 A | * | 10/1971 | Dent et al. ..................... 73/159 |
| 3,618,372 A | * | 11/1971 | Beckstrom ................... 73/839 |
| 3,675,475 A | | 7/1972 | Weinstein |
| 3,713,328 A | | 1/1973 | Aritomi |
| 3,798,960 A | | 3/1974 | Glass |
| 3,804,092 A | * | 4/1974 | Tunc .......................... 604/364 |
| 3,805,598 A | | 4/1974 | Corcoran |
| 3,818,751 A | | 6/1974 | Karper et al. |
| 3,835,697 A | * | 9/1974 | Schneider et al. ................ 73/7 |
| 3,838,596 A | * | 10/1974 | Neuenschwander .......... 73/816 |

(List continued on next page.)

FOREIGN PATENT DOCUMENTS

| | | |
|---|---|---|
| CA | 2112792 | 7/1994 |
| EP | 0 317 356 A2 | 5/1989 |
| EP | 1 158 290 A2 | 11/2001 |
| JP | 402297040 A | 12/1990 |
| WO | WO 96/11878 | 4/1996 |
| WO | WO 98/15501 | 4/1998 |
| WO | WO 99/18431 | 4/1999 |
| WO | WO 00/17413 | 3/2000 |
| WO | WO 00/23921 | 4/2000 |
| WO | WO 0036410 | 6/2000 |
| WO | WO 00/40331 | 7/2000 |
| WO | WO 00/51720 | 9/2000 |
| WO | WO 00/67086 | 11/2000 |
| WO | WO 01/79949 A2 | 10/2001 |

OTHER PUBLICATIONS

Young, W.C., Roark's Formulas for Stress and Stain, 1989.

Osterberg, Peter M. and Stephen D. Senturia, "M–TEST: A Test Chip for MEMS Material Property Measurement Using Electrostatistically Actuated Test Structures," Journal of Microelectromechanical Systmes, vol. 6, No. 2, Jun. 1997.

Kim, J.O. and B. Lewis Slaten, "Objective Assessement of Fabric Handle in Fabrics Treated With Flame Retardants," Journal of Testing and Evaluation, JTEVA, vol. 24, No. 4, Jul. 1996, pp. 223–228.

(List continued on next page.)

*Primary Examiner*—Hezron Williams
*Assistant Examiner*—David A. Rogers
(74) *Attorney, Agent, or Firm*—Dobrusin & Thennisch PC

(57) ABSTRACT

A method for screening fabric handle of an array of fabric samples (i.e., a plurality of fabric materials) comprising providing an array of at least two fabric samples, protruding the fabric samples through openings, and monitoring response of said fabric samples to the protrusions.

47 Claims, 8 Drawing Sheets

U.S. PATENT DOCUMENTS

| | | | |
|---|---|---|---|
| 3,849,874 | A | 11/1974 | Jeffers |
| 3,895,513 | A | 7/1975 | Richardson |
| 3,908,441 | A | 9/1975 | Virloget |
| 3,933,032 | A | 1/1976 | Tschoegl |
| 4,103,550 | A * | 8/1978 | Alley et al. .................. 73/789 |
| 4,229,979 | A | 10/1980 | Greenwood |
| 4,447,125 | A | 5/1984 | Lazay et al. |
| 4,517,830 | A | 5/1985 | Gunn et al. |
| 4,567,774 | A | 2/1986 | Manahan et al. |
| 4,570,478 | A | 2/1986 | Soong |
| 4,599,219 | A | 7/1986 | Cooper et al. |
| 4,602,501 | A | 7/1986 | Hirata |
| 4,605,589 | A | 8/1986 | Orphanides |
| 4,680,958 | A | 7/1987 | Ruelle et al. |
| 4,685,328 | A | 8/1987 | Huebner et al. |
| 4,699,000 | A | 10/1987 | Lashmore et al. |
| 4,715,007 | A | 12/1987 | Fujita et al. |
| 4,740,078 | A | 4/1988 | Daendliker et al. |
| 4,749,854 | A | 6/1988 | Martens |
| 4,776,202 | A * | 10/1988 | Brar et al. .................. 73/12.13 |
| 4,789,236 | A | 12/1988 | Hodor et al. |
| 4,793,174 | A | 12/1988 | Yau |
| 4,829,837 | A | 5/1989 | Telfer |
| 4,893,500 | A | 1/1990 | Fink-Jensen |
| 4,899,575 | A | 2/1990 | Chu et al. |
| 4,899,581 | A | 2/1990 | Allen et al. |
| 4,932,270 | A | 6/1990 | Lurie et al. |
| 4,975,320 | A | 12/1990 | Goldstein et al. |
| 5,008,081 | A | 4/1991 | Blau et al. |
| 5,051,239 | A | 9/1991 | von der Goltz |
| 5,092,179 | A | 3/1992 | Ferguson |
| 5,115,669 | A | 5/1992 | Fuller et al. |
| 5,142,900 | A | 9/1992 | Duke |
| 5,193,383 | A | 3/1993 | Burnham et al. |
| 5,236,998 | A | 8/1993 | Lundeen et al. |
| 5,269,190 | A | 12/1993 | Kramer et al. |
| 5,271,266 | A | 12/1993 | Eschbach |
| 5,272,912 | A | 12/1993 | Katsuzaki |
| 5,280,717 | A | 1/1994 | Hoseney et al. |
| 5,303,030 | A | 4/1994 | Abraham et al. |
| 5,305,633 | A | 4/1994 | Weissenbacher et al. |
| 5,398,885 | A | 3/1995 | Andersson et al. |
| 5,437,192 | A | 8/1995 | Kawamoto et al. |
| 5,438,863 | A | 8/1995 | Johnson |
| 5,452,614 | A | 9/1995 | Kato et al. |
| 5,452,619 | A | 9/1995 | Kawanabe et al. |
| 5,481,153 | A | 1/1996 | Turner |
| 5,517,860 | A | 5/1996 | Lin et al. |
| 5,520,042 | A | 5/1996 | Garritano et al. |
| 5,532,942 | A | 7/1996 | Kitamura et al. |
| 5,610,325 | A | 3/1997 | Rajagopal et al. |
| 5,614,662 | A | 3/1997 | Hallan et al. |
| 5,626,779 | A | 5/1997 | Okada |
| 5,699,159 | A | 12/1997 | Mason |
| 5,700,953 | A | 12/1997 | Hlady et al. |
| 5,723,792 | A | 3/1998 | Miyazaki |
| 5,728,532 | A | 3/1998 | Ackley |
| 5,756,883 | A | 5/1998 | Forbes |
| 5,764,068 | A | 6/1998 | Katz et al. |
| 5,776,359 | A | 7/1998 | Schultz et al. |
| 5,790,983 | A * | 8/1998 | Rosch et al. .................. 2/69 |
| 5,795,989 | A * | 8/1998 | Simmons et al. .................. 73/7 |
| 5,799,103 | A | 8/1998 | Schneider et al. |
| 5,817,947 | A | 10/1998 | Bergerus |
| 5,821,407 | A | 10/1998 | Sekiguchi et al. |
| 5,847,283 | A | 12/1998 | Finot et al. |
| 5,877,428 | A | 3/1999 | Scolton |
| 5,892,157 | A | 4/1999 | Syre |
| 5,922,967 | A | 7/1999 | Motoyama |
| 5,959,297 | A | 9/1999 | Weinberg et al. |
| 5,985,356 | A | 11/1999 | Schultz et al. |
| 5,999,887 | A | 12/1999 | Giannakopoulos et al. |
| 6,004,617 | A | 12/1999 | Schultz et al. |
| 6,010,616 | A | 1/2000 | Lewis et al. |
| 6,013,199 | A | 1/2000 | McFarland et al. |
| 6,030,917 | A | 2/2000 | Weinberg et al. |
| 6,033,913 | A | 3/2000 | Morozov et al. |
| 6,034,240 | A | 3/2000 | La Pointe |
| 6,034,775 | A | 3/2000 | McFarland et al. |
| 6,040,193 | A | 3/2000 | Winkler et al. |
| 6,043,317 | A | 3/2000 | Mumick et al. |
| 6,043,363 | A | 3/2000 | LaPointe et al. |
| 6,045,671 | A | 4/2000 | Wu et al. |
| 6,050,138 | A | 4/2000 | Lynch et al. |
| 6,050,139 | A | 4/2000 | Bousfield et al. |
| 6,087,181 | A | 7/2000 | Cong |
| 6,092,414 | A | 7/2000 | Newman |
| 6,124,476 | A | 9/2000 | Guram et al. |
| 6,149,882 | A | 11/2000 | Guan et al. |
| 6,151,123 | A | 11/2000 | Nielsen |
| 6,157,449 | A | 12/2000 | Hajduk |
| 6,175,409 | B1 | 1/2001 | Nielsen et al. |
| 6,177,528 | B1 | 1/2001 | LaPointe et al. |
| 6,182,499 | B1 | 2/2001 | McFarland et al. |
| 6,187,164 | B1 | 2/2001 | Warren et al. |
| 6,203,726 | B1 | 3/2001 | Danielson et al. |
| 6,225,487 | B1 | 5/2001 | Guram |
| 6,225,550 | B1 | 5/2001 | Hornbostel et al. |
| 6,242,623 | B1 | 6/2001 | Boussie et al. |
| 6,248,540 | B1 | 6/2001 | Weinberg et al. |
| 6,260,407 | B1 | 7/2001 | Petro et al. |
| 6,265,226 | B1 | 7/2001 | Petro et al. |
| 6,265,601 | B1 | 7/2001 | Guram et al. |
| 6,268,513 | B1 | 7/2001 | Guram et al. |
| 6,294,388 | B1 | 9/2001 | Petro |
| 6,296,771 | B1 | 10/2001 | Miroslav |
| 6,306,658 | B1 | 10/2001 | Turner et al. |
| 6,315,923 | B1 | 11/2001 | Devenney et al. |
| 6,324,251 | B1 * | 11/2001 | Kuwabara .................. 378/48 |
| 6,326,090 | B1 | 12/2001 | Schultz et al. |
| 6,489,776 | B1 | 12/2002 | Stowe et al. |

Grover, G. et al., "A Screening Technique for Fabric Handle", J. Text. Inst., 1993, 84 No. J. Textile Institute, pp. 486–494.

Pan, Ning and K.C. Yen, "Physical Interpretations of Curves Obtained Through the Fabric Extraction Process for Handle Measurement," Textile Research Journal 62(5), pp. 279–290 (1992).

"Handle–O–Meter", Thwing–Albert Instrument Company, Philadelphia, PA.

Rafeel, Mastura and Jiang Liu, "An Empirical Model for Fabric Hand" Textile Research Journal 62, 1, pp. 31–38 (1991).

Ali, S.I. and Shahida Begum, "Fabric Softeners and Softness Perception", Ergonomics, v.37, No. 5, pp. 801–806 (1994).

The family of applications for U.S. Appl. No. 09/156,827 entitled "Formation of Combinatorial Arrays of Materials Using Solution–Based Methodologies" (Giaquinta et al.) filed Sep. 18, 1998.

U.S. Appl. No. 09/579,338 entitled "Rheo–Optical Indexer and Method of Screening and Characterizing Arrays of Materials" (Carlson et al.) filed on May 25, 2000.

U.S. Appl. No. 09/939,404 entitled "High Throughput Mechanical Property and Bulge Testing of Material Libraries," (D. Hajduk et al.) filed on Aug. 24, 2001.

U.S. Appl. No. 09/939,252 entitled "High Throughput Mechanical Rapid Serial Property Testing of Material Libraries," (P. Mansky) filed on Aug. 24, 2001.

U.S. Appl. No. 09/939,149 entitled "High Throughput Rheological Testing of Materials Libraries Using ," (P. Mansky et al.) filed on Aug. 24, 2001.

U.S. Appl. No. 09/939,263 entitled "High Throughput Mechanical Property Testing of Materials Libraries Using Capacitance," (D. Hajduk et al.) filed on Aug. 24, 2001.

U.S. Appl. No. 09/938,994 entitled "High Throughput Mechanical Property Testing of Materials Libraries Using a Piezoelectric," (D. Hajduk) filed on Aug. 24, 2001.

The family of applications for U.S. Appl. No. 09/580,024 entitled "Instrument for High Throughput Measurement of Material Physical Properties and Method of Using Same," (Carlson, et al.) filed on May 26, 2000.

U.S. Appl. No. 09/801,165 entitled "Method and Apparatus for Characterizing Materials By Using a Mechanical Resonator" filed Mar. 7, 2001.

U.S. Appl. No. 09/578,997 entitled "High Throughput Viscometer and Method of Using Same" filed May 25, 2000.

U.S. Appl. No. 09/420,334 entitled "Graphic Design of Combinatorial Material Libraries" (Lacy, et al.) filed on Oct. 18, 1999.

U.S. Appl. No. 09/305,830 titled "Synthesizing Combinatorial Libraries of Materials" (Rust, et al.) filed on May 5, 1999.

U.S. Appl. No. 09/550,549 entitled "Automated Process Control And Data Management System And Methods" (Crevier, et al.) filed on Apr. 14, 2000.

U.S. Appl. No. 09/755,623 entitled "Laboratory Database System and Methods for Combinatorial Materials Research" (Dorsett, Jr., et al.) filed on Jan. 5, 2001.

The family of application of U.S. Appl. No. 09/227,558 entitled, "Apparatus and Method of Research for Creating and Testing Novel Catalysts, Reactions and Polymers" (Turner et al.) filed Jan. 8, 1999.

U.S. Appl. No. 09/235,368 entitled "Polymerization Method From the Combinatorial Synthesis and Analysis of Organometallic Compounds and Catalysts" (Weinberg et al.) filed on Jan. 21, 1999.

U.S. Appl. No. 60/122,704 entitled "Controlled, Stable Free Radical Emulsion and Water–Based Polymerizations" (Klaerner et al.) filed on Mar. 9, 1999.

The family of applications of U.S. Appl. No. 09/567,598 entitled "Polymer Libraries on a Substrate, Method for Forming Polymer Libraries on a Substrate and Characterization Methods and Same" (Boussie et al.) filed May 10, 2000.

The family of applications for U.S. Appl. No. 09/174,856 titled "Graphic Design of Combinatorial Material Libraries" (Lacy, et al.) filed on Oct. 19, 1998.

Odian, Principles of Polymerization, 3rd Ed., JOhn Wiley & Sons, Inc. (1991).

Timoshenko, S., Theory of Plates and Shells, McGraw–Hill, New York 1940.

"DMA 2980 Dynamic Mechanical Analyer," http://www.tainst.com/dma2.html, Dec. 29, 2000.

"Introducing the NEW DMTA V!", http://www.rheometricscientific.com/dmtaV.htm, Dec. 29, 2000.

"Standard Test Method for Rubber Property–Intrenational Hardness," American Society for Testing and Materials.

Amitay–Sadovsky, Ella and H. Daniel Wagner, "Evaluation of Young's Modulus of Polymers from Knoop Microindentation Tests" Polymer Communications, 1998, vol. 39, No. 11, pp. 2387–2390.

Calleja, F.J. Balta, "Microhardness Studies of Polymers and Their Transitions" TRIP, Dec. 1994, vol. 2, No. 12, pp. 419–425.

Bowlt, C., "A Simple Capillary Viscometer" Physics Education, Mar. 1975, vol. 10, No. 2, pp. 102–103.

LaCombe, Robert H. and Jeremy Greenblatt, "Mechanical Properties of Thin Polyimide Films" pp. 647–668.

Shinzaki, D.M. and Y. Lu, "Micro–Indentation Relaxation Measurements in Polymer Thin Films" Journal of Electronic Materials, 1997, vol. 26, No. 7, pp. 852–858.

Wierenga, P.E. and A.J.J. Franken, "Ultramicroindentation Apparatus for the Mechanical Characterization of Thin Films" J. Appl . Phys., Jun. 15, 1984, 55 (12).

European Search Report datd Dec. 10, 2001.

* cited by examiner

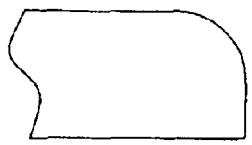
Fig-3D
Fig-3E
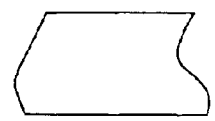
Fig-3F
Fig-3G
Fig-3H
Fig-3I
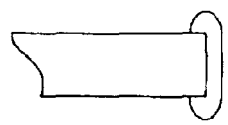
Fig-3J

HIGH THROUGHPUT FABRIC HANDLE SCREENING

TECHNICAL FIELD

The present invention generally relates to the field of textile material characterization. In particular, the invention relates to high throughput fabric handle screening.

BACKGROUND OF THE INVENTION

Fabric handle refers to the tactile sensations associated with fabrics. Fabric handle is a combination of various fabric characteristics such as smoothness, firmness, fullness, crispness and hardness. The textile industry is very interested in assessing fabric handle for their products because it has a strong impact on consumer preference for a particular textile product. Historically, fabric handle has been assessed by individuals using their own physical senses. In an effort to avoid errors associated with the subjectivity involved in such assessment, objective assessment methods and instruments have been introduced to measure the mechanical properties associated to fabric handle such as bending modulus, shear stiffness, compression, friction, and extensibility. Studies have shown that there is a good correlation of these mechanical properties with human tactile response. See Kim, J. O. and Slaten, B. L., "Objective Assessment of Fabric Handle in Fabrics Treated With Flame Retardants," *Journal of Testing and Evaluation*, JTEVA, Vol. 24, No. 4, July 1996, pp. 223–228; G. Grover, Sultan, M. A., and Spivak, S. M., "A Screening Technique for Fabric Handle", *J. Text Inst*, 1993, 84 No. J. Textile Institute, pp. 486–494. Nevertheless, these objective assessment methods and instruments present a multitude of challenges. They are time consuming in that they lack the ability to screen the mechanical properties associated with fabric handle of several fabric materials in rapid succession or in parallel. Thus, challenges are presented for forming systems that can quickly process and screen (either in parallel or in serial succession) mechanical properties associated with fabric handle of many fabric materials.

SUMMARY OF THE INVENTION

The present invention provides methods for high throughput fabric handle screening that address many of the challenges encountered when using conventional methods and instruments. For example, the disclosed methods can screen for the mechanical properties associated with fabric handle of an array of fabric samples in parallel and/or rapid serial and can perform screens on small samples of fabric materials. Thus, the present invention provides methods of screening the mechanical properties associated with fabric handle of a plurality of fabric samples (e.g., assembled together in an array).

In accordance with one preferred embodiment of the present invention, an array of fabric samples is provided and all or at least two of the samples are protruded simultaneously. The responses of each of the samples to the protrusions are monitored for gathering information related to its mechanical properties associated with fabric handle such as its bending modulus, shear stiffness, compression, friction, and extensibility, or the like.

In another preferred embodiment, an array of fabric samples is provided and the samples are protruded one at a time in a rapid serial fashion. The responses of each of the samples to the protrusions are monitored for gathering information relating to its mechanical properties associated with fabric handle such as its bending modulus, shear stiffness, compression, friction, and extensibility or the like.

BRIEF DESCRIPTION OF THE DRAWINGS

FIGS. 3C–J each shows a cross sectional view of an opening for which an array sample is protruded through during high throughput fabric handle screening.

DETAILED DESCRIPTION OF THE PREFERRED EMBODIMENT

The present invention comprises methods for high throughput screening of a plurality of fabric samples for mechanical properties generally associated with fabric handle, by measuring the responses of individual array samples to protrusions. In a preferred embodiment, a plurality of fabric samples is assembled together to define an array of fabric samples. The fabric samples materials in the array can be the same or different materials. The array can be supported on a single common support or a plurality of assembled supports. A further detailed description of the array of fabric samples is provided below in the section titled "Preparation of an Array of Fabric Samples".

As used herein, the term "protrusions" generally refers to controlled forces or displacements applied by a probe, or device to a fabric sample for causing at least a portion of the fabric sample to be forced through an opening defined in a plane of a sample support member. Preferably a protrusion as used herein will be of sufficient magnitude for effecting such sample manipulation without piercing the sample. In some embodiments, however, it is contemplated that piercing will or desirably should occur.

Figure 1:
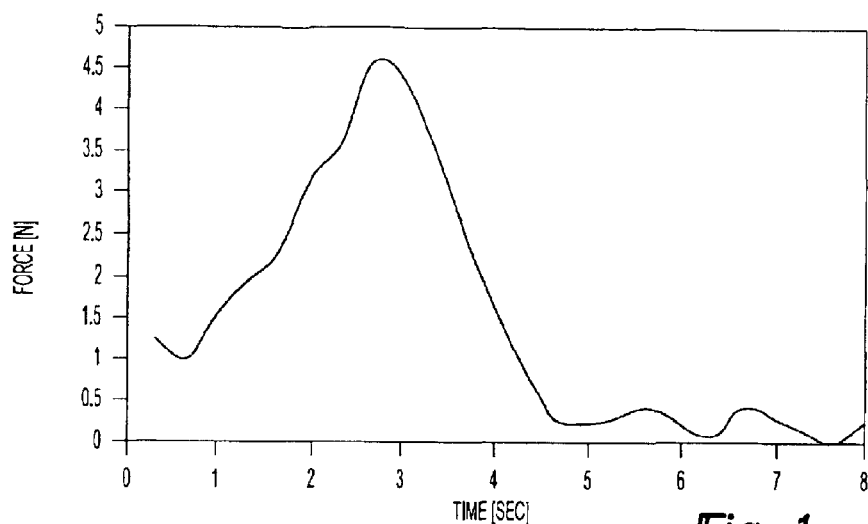
FIG. 1 shows a load-displacement curve obtained during fabric handle screening from an individual fabric sample of an array.

In accordance with effectuating one type of preferred protrusion, as the sample is passed through the opening (i.e., pushed out of the normal plane of the opening), it is expected to become folded, sheared, bent, compressed, elongated, or rubbed against the interior wall of the support member defining the opening. Responses to the protrusions are measured and recorded as a load-displacement curve as shown in FIG. 1. The load displacement curve yields the mechanical properties associated with or bearing upon fabric handle such as bending modulus, shear stiffness, compression, friction, and extensibility, or the like.

Preparation of an Array of Fabric Samples

The number of fabric samples in an array may vary depending on the embodiment being practiced. In some embodiments, an array will comprise four or more, eight or more, sixteen or more, twenty-four or more, or forty-eight or more fabric materials. Those of skill in the art will appreciate from this specification that members of the array may be the same or different materials. Fabric samples may be woven or unwoven, coated or uncoated, or aggregated with a suitable binder or not. The present invention is not limited to any particular type of fabric material and may include a woven material (e.g., batiste, chiffon, net, voile, organza, georgette, challis, chambray, charmeuse, crepe, dotted swiss, handkerchief linen, satin, eyelet, lace, velvet, taffeta, metallic, gauze, jacquard, gingham, percale, seersucker, broadcloth, brocade, linen, pique, shantung, chintz, velveteen, polyester blend acrylic, fleece, gabardine, denim, twill, corduroy, terry, velour, canvas, duck, percale, tergal, flannel, lame, tricotine, etc.), a non-woven material (e.g., felt, fusibles, interfacing, etc.), a knit material (e.g., atlas, jersey, pointelle, raschel, mesh, panne velvet, tricot, rib knit, double knit, interlock, intarsia, etc.), a pile material (e.g., chenille, chinchilla, faux fur, frieze, grospoint, tubular, etc.), a blend material (e.g., cotton/silk blend, cotton/wool blend, etc.), a composite material (e.g., laminated, etc.), or a combination thereof. The fabric materials can be natural (e.g., cotton, silk, linen, wool, hemp, ramie, jute, etc.), synthetic (e.g., acetate, acrylic, lastex, nylon, polyester, rayon, etc.), or combination thereof. They can also be acrylic coated, airo finished, bleached, resin treated, sanded, scented, sheared, silver coated, wax coated, stonewashed, bonded, enzyme washed, flocked, glazed, mercerized, milled/fulled, and subject to other textile treatments for color, texture, bacterial resistant, soil resistant, oil repellent, flame resistant, pill resistant water resistant, mildew resistant, water repellant, wrinkle resistant, or ultra violet resistant, etc. Standards (such as calibration standards) or blanks may be employed in the array for known scientific purposes. In this regard, the present invention is particularly attractive for the screening of effects of variations of textile treatments and/or additives (e.g., surfactants, fillers, reinforcements, flame retardants, colorants, environmental protectants, other performance modifiers, control agents, plasticizers, cosolvents, accelerators, etc.) upon the fabric handle of a fabric material.

Relative comparison of the fabric hand of array members (including for instance the comparison with a standard or blank) is a useful embodiment of this invention. Quantitative measurements of fabric hand are also provided by the present invention. The quantitative measurements allow comparison of fabric hand between the array members and other fabric materials not included in the array. As will be appreciated from the discussion elsewhere herein, in one particular embodiment, different material samples are compared with each other (quantitatively or qualitative, according to defined criteria) and their relative performance is ranked. In another particular embodiment, different material samples are compared to determine whether a specific response has occurred in any of the material samples. From the analysis of the materials, sub-sets of materials can be identified for further study or for production in bulk-scale quantities, such as for commercial application.

In regard to typical non-woven materials, and optionally to woven or other materials, it is preferred that fibers are aggregated in a generally cohesive manner. By way of example, to provide cohesion, it is preferred that the material is aggregated together with a suitable binder, (e.g., by applying in a wet state an emulsion containing waxes or polymers that, when dried, will form a continuous phase around the non-woven fibers). A particularly preferred binder for use in the present invention is an aqueous emulsion including a polymer (more preferably a copolymer). A more preferred binder also may include, a stabilizer, a surfactants, a crosslinking agent, or other suitable agent to impart mechanical strength to the system (e.g., once it has been exposed to elevated temperature (~150° C.)). The binder may add 1 to 99, preferably 5 to 50, more preferably 10–30 percentage weight to the fabric material.

What may vary from binder to binder are (1) the monomers used in the polymerization; (2) the order in which they are attached (random or blocky); (3) the surfactants; and (4) any other additives that may give the system unique characteristics (e.g., something that is sensitive to the presence of ions). One preferred binder includes an olefin, a vinyl ester, or a combination thereof, and an example of such a preferred binder is a copolymer of ethylene and vinyl acetate in an emulsion with various stabilizers. For more examples of suitable binders, see U.S. Pat. Nos. 4,605,589, 4,975,320 and 6,043,317. It is preferred that the binder should generally be uniformly distributed throughout the non-woven material, but it also may be randomly distributed. Such uniform distribution can be achieved using any number of conventional techniques. For example, the non-woven material immersed with the binder is passed through spaced opposing surfaces such as rubber-coated rollers with a self-adjusting gap to squeeze out any excess binder and provide uniform distribution. Depending on the nature of the binder (e.g., whether it contains any cross-linkable polymers), a drying step and/or a curing step can be used to process the non-woven material treated with the binder.

In accordance with the teachings of the present invention, it may also be possible to employ the present invention for analyzing the effects of the use of different binders from sample to sample. Thus, in an array of samples, binders employed may be the same or different.

The shape and size of each array sample can generally vary, depending on the particular characterization protocols and systems used to analyze the sample. It is generally contemplated that arrays of samples will be mounted for screening in or on a suitable support structure, namely a sample holder. Typically, the sample holder will have at least one and more preferably a plurality of openings defined therein. Thus, in one preferred embodiment, the sample size will be larger than the opening through which it will be forced by a probe during screening. It is preferred that the sample is at least about 2 times larger than the opening, more preferred at least about 5 times larger than the opening, and most preferred about 10 times larger than the opening. It is appreciated that the present invention advantageously permits for attaining reliable data with relatively small samples, but the actual sample size is not critical. Typical sample sizes can range from about 8 mm to about 18 mm, more preferred from about 12 mm to about 18 mm, and most preferred from about 15 mm to about 17 mm. Larger diameters are also possible.

The Parallel Dynamic Mechanical Analyzer

Figure 2:
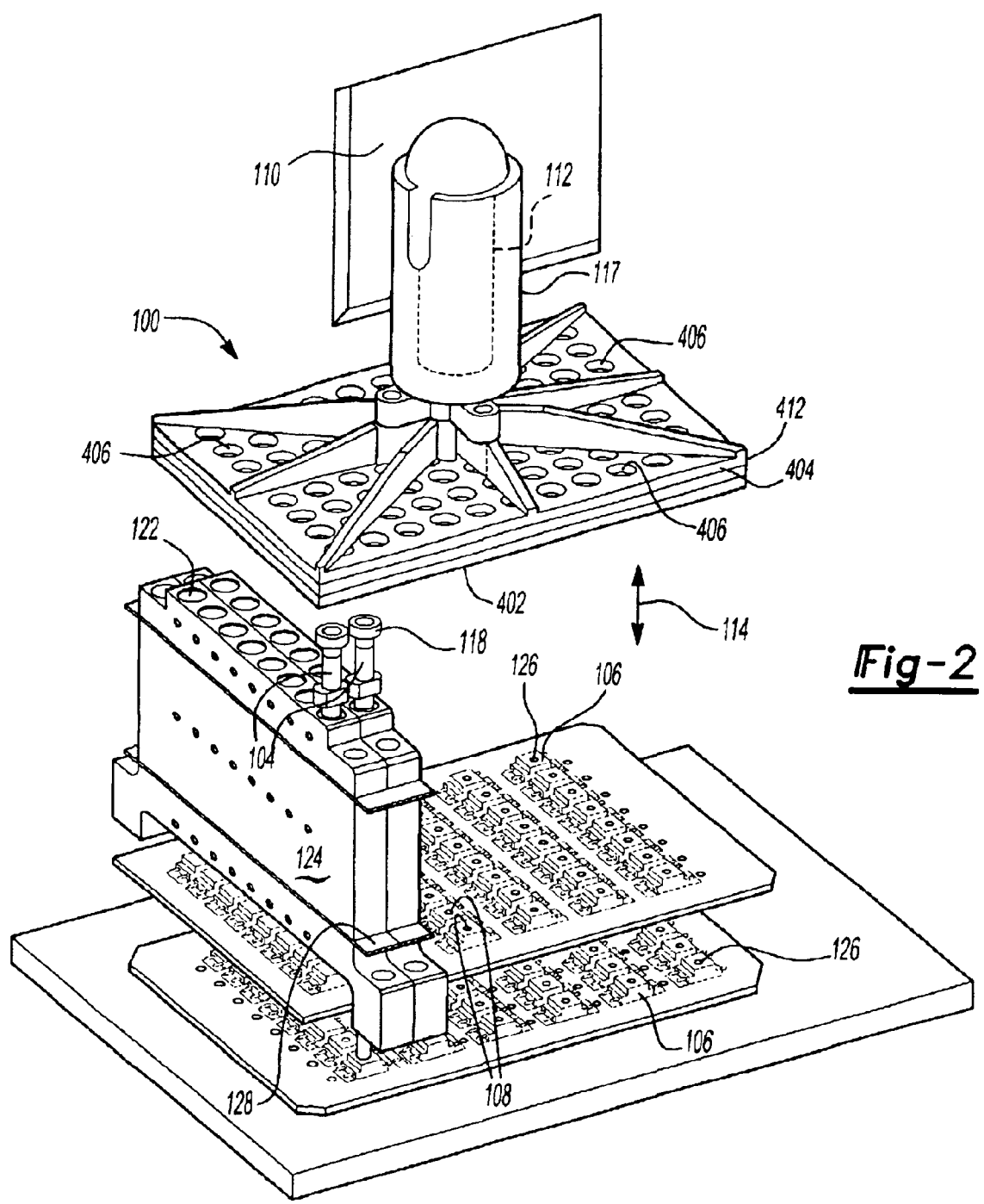
FIG. 2 shows a perspective view of one embodiment of a parallel dynamic mechanical analyzer that can be used for high throughput fabric handle screening.

FIG. 2 shows a perspective view of one instrument suitable for property analysis (i.e., screening), and specifically, a parallel dynamic mechanical analyzer (PDMA) 100 that can be used to conduct high throughput fabric handle screening of an array of fabric samples 230 by measuring responses of the array 230 to protrusions. Detailed description of the PDMA 100 is described in commonly owned and co-pending U.S. patent application Ser. No. 09/580,024 titled "Instrument for High Throughput Measurement of Material Physical Properties and Method of Using Same," filed on May 26, 2000, which is herein incorporated by reference. Generally, the PDMA 100 includes a sample holder 102 for containing the array 230, probes 104 for protruding the array 230, and sensors 106 (e.g., force sensors) for measuring the array's 230 responses to the protrusions. The sample holder may be a single integrated unit or a plurality of assembled components; likewise it may comprise a single opening in a first substrate, which is translatable (e.g., by robot arm) relative to a second substrate for holding sample.

Figure 3A:
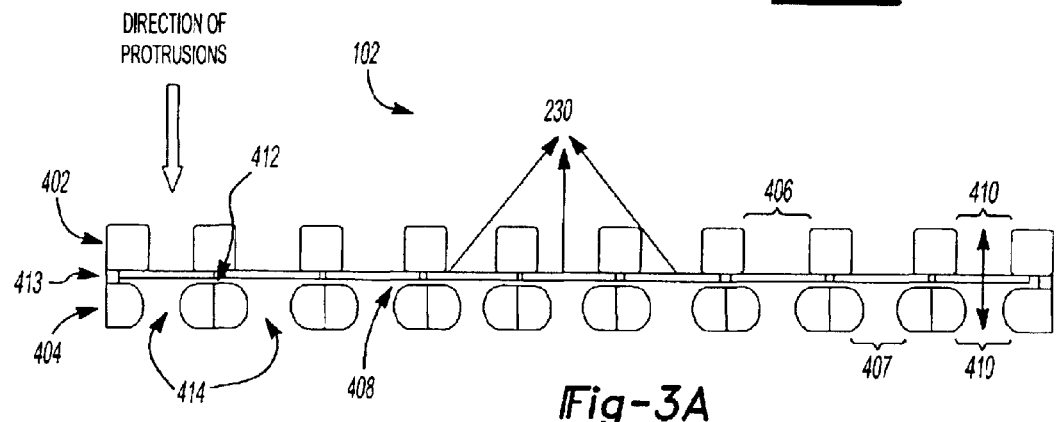
FIGS. 3A–B each shows a cross sectional view of a sample holder containing an array of fabric samples for fabric handle screening that can be used in a parallel dynamic mechanical analyzer for high throughput fabric handle screening.
Figure 3B:
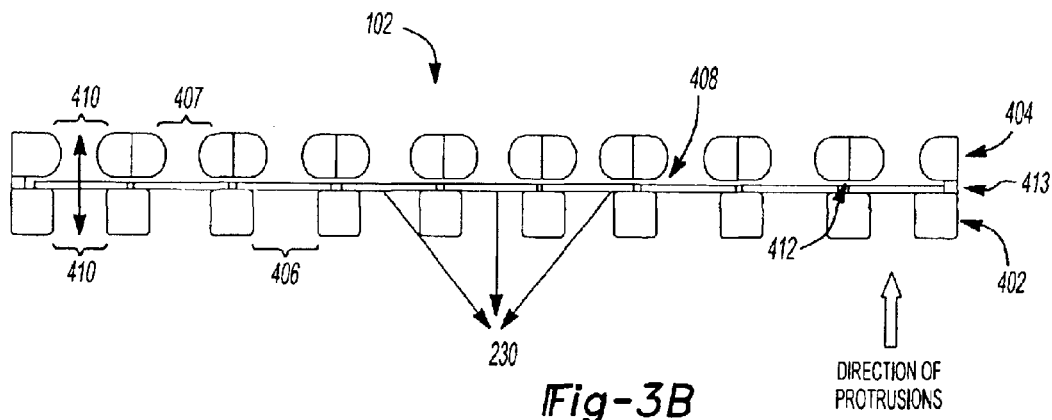

FIG. 3A shows a cross-sectional view of one preferred sample holder 102 which is comprised of a first plate 402 having a plurality of through-holes 406 and a second plate 404 having a plurality of openings 407 wherein the through-holes 406 and the openings 407 are aligned with each other forming tunnels 410 within the sample holder 102. Since the array 230 are protruded through the openings 407, their size and shape can affect the fabric handle measurements and are taken into consideration in measuring the fabric handle of the array 230. For instance, each of the openings 407 preferably is large enough for the array sample 230 to collapse upon itself, while still maintaining a portion of itself in physical contact with the walls of the opening 407 during the protrusions. Referring to FIG. 3A, one preferred leading edge 408 to the opening 407 must allow for a smooth transition for the sample 230 to transfer from a flat state to the bent and folded state which occurs during the protrusions. Thus, it is preferred that the opening 407 is constructed of a smooth material or coated with a smooth material (e.g., a plastic layer, a coating, or the like). Although the openings 407 can be any shape and/or size, it is preferred that they are funnel-shaped or otherwise a rounded or a tapered periphery with a diameter at the top of each funnel that is twice of the bottom diameter, and with the height of the sloped section at least equal to the height of the straight section. For examples of other preferred embodiments of the openings 407 that may be used during fabric handle screens, see FIGS. 3C–J. Other variations or combinations of such structures are also possible. The through-holes 406 can also be any shape or size as long as they do not restrict or inhibit the protrusions of the array 230 by the probes 104. Furthermore, depending on the direction of the protrusions, the first plate 402 may be placed above the second plate 404 with its openings 407 as shown in FIG. 3A or vice versa as shown in FIG. 3B.

Figure 3C:
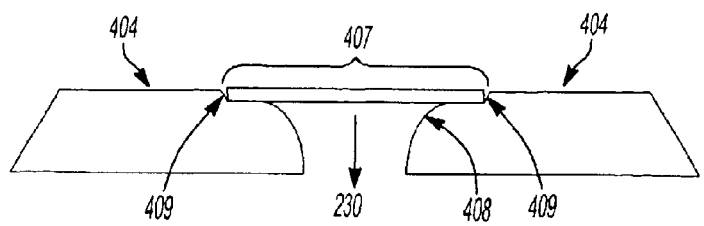

Referring to FIG. 3A, a gap of suitable size 412, e.g., preferably about 1 mm, more preferably about 3 mm, exists between the first plate 402 and the second plate 404. The gap 412 can be formed by any number of art disclosed techniques. For example, spacers 413 such as beads or two standard washers (e.g., 0.5 mm each) can be placed between the first plate 402 and the second 404 to create a gap of approximately 1 mm. The array 230 is placed between the first plate 402 and the second plate 404 of the sample holder 102 with the individual array samples 230 confined to specific locations 414 on the sample holder 102. Referring to FIG. 3C, it is preferred that each opening 407 is surrounded by an indentation 409 in the second plate 404 that restricts any horizontal movement of its respective sample 230. It is also preferred that there is a one to one correspondence between the specific locations 414 and the openings 407. Additionally, it is preferred that the samples 230 do not overlap each other but each sample 230 is sized to include and extend beyond the regions defined by the diameter of the opening 407. It is preferred that each sample 230 is at least about 2 times larger than the diameter of the opening 407, more preferred at least about 5 times larger than the diameter of the opening 407, and most preferred about 10 times larger than the diameter of the opening 407. The particular sample holder 102 shown in FIG. 2 and FIG. 3 contains an 8-by-12 rectangular array of fabric samples 230 located on 9 mm centers. However, the sample holder 102 can be designed to contain any number of samples in an array. For example, the sample holder 102 can be designed to contain 4 or more, 8 or more, 16 or more, 24 or more or 48 or more samples in an array. Those of skill in the art will appreciate that this is simply a matter of design choice and the invention herein is not limited to the specific embodiments described in detail.

The PDMA 100 generally has as many probes 104 as desired. For example there may be as many as there are samples in the array 230, although for clarity, FIG. 2 shows only two probes 104. In the embodiment shown in FIG. 2, the probes 104 have the same lateral spacing as the tunnels 410 or openings 407 so that one probe 104 is associated with one opening 407 or sample 230. Alternatively, the PDMA may employ fewer probes 104 than samples in the array 230, so that a group of probes 104 protrudes multiple samples 230. It is preferred that the PDMA 100 includes a translation mechanism capable of three-dimension motion, which is attached to this group of probes 104 or to the sample holder 102 to allow high throughput serial-parallel screening. Alternatively, there may be more probes 104 than samples in the array 230. Alternatively, there may be only one probe 104 and the PDMA 100 includes a translation mechanism capable of three-dimensional motion, which is attached to the single probe 104 or to the sample holder 102 to allow high throughput screening in a rapid serial fashion.

The PDMA 100 includes at least one actuator for moving the probes 104 and the samples 230 in relation to each other. In one preferred embodiment, the actuators are attached to the probes 104 and the samples 230 remain stationary. In another preferred embodiment, the actuators are attached to the sample holder 102 and the probes remain stationary. In yet another preferred embodiment, both the probes 104 and the sample holder 102 have actuators attached allowing them to both become non-stationary. In an exemplary preferred embodiment, the PDMA 100 includes first 110 and second 112 translation actuators for displacing the array 230 in a direction normal 114 to surfaces containing the array 230 and the ends 116 of the probes 104. The first translation actuator 110, which is attached to the sample holder 102 via a housing 117 that surrounds the second translation actuator 112, provides relatively coarse displacement of the sample holder 102. A useful first translation actuator 110 includes a motorized translation stage available from POLYTEC PI under the trade name M-126 Translation Stage, which has a translation range of 25 mm and a resolution of 0.1 μm. The second translation actuator 112, which is attached directly to the sample holder 102, provides relatively fine displacement of the sample holder 102. A useful second translation actuator 112 includes a preloaded piezoelectric stack available from Polytec PI under the trade name P-753 LISA Linear PZT Stage Actuator, which has a translation range of 30 mm and can provide a 100-N pushing force and a 20-N pulling force. The PDMA 100 typically controls the first 110 and second 112 translation actuators using a DC motor controller and an amplifier/position servo controller, respectively, which are linked to a suitable general-purpose computer (not shown). In an alternative embodiment, the first 110 translation actuator is mounted on an x-y translation stage (not shown), which allows movement of the sample holder 102 in a direction substantially parallel to the surfaces containing the array 230 and the ends of the probes 104. This latter embodiment is useful when the sample holder 102 must be moved laterally to align different groups of array samples 230 with the probes 104 during screening—i.e., when the PDMA employs fewer probes 104 than samples in the array 230 and the probes 104 are stationary.

Each of the probes 104 includes a test fixture 118 that contacts one of the sensors 106 through a solid or composite shaft 120 shown in phantom in FIG. 2. Each shaft 120 passes through an aperture 122 in an isolation block module 124 that separates the probe test fixture 118 from the sensor 106. For clarity, FIG. 2 shows only two isolation block modules 124, although this embodiment of the PDMA 100 ordinarily includes twelve such modules 124—one isolation block module 124 for each row of eight probes 104. Alternatively, the PDMA may include a single isolation block for separating the probe test fixtures 118 from the sensors 106. For reliable measurements, each test fixture 118 should contact its associated sample 230 in a specific location 108 on the sample holder 102. This requires a mechanism for locating the composite shaft 120 along a line extending from the center 126 of a particular sensor 106, normal to the surface of the array 230. Although conventional linear bearings can be used to align the composite shaft 120, friction between the linear bearings and the shaft 120 limits the displacement resolution at low force levels. In addition, the PDMA can also use air bearings, but the size and expense of air bearings often make them impractical for use with a PDMA employing relatively large numbers of probes 104.

Figure 4:
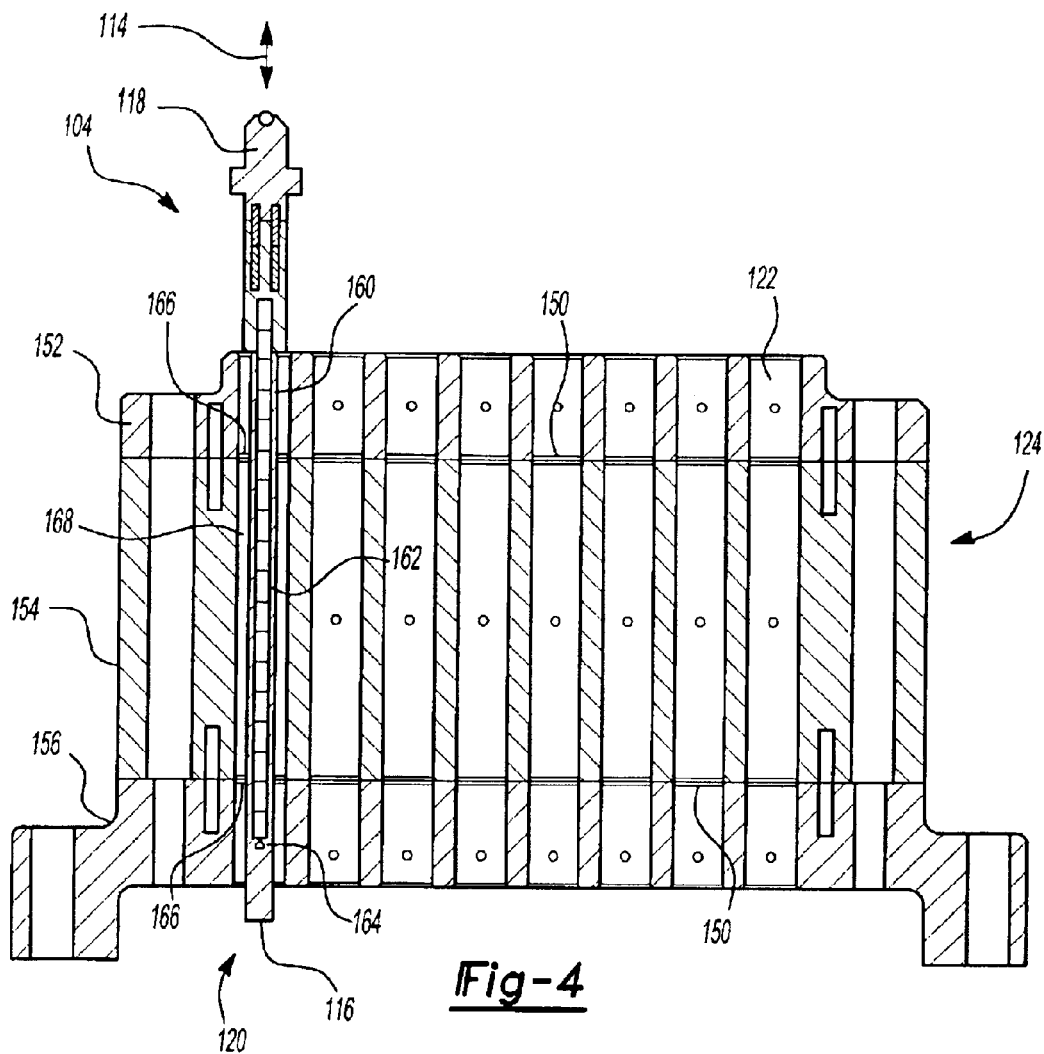
FIG. 4 shows a cross sectional view of an isolation block module that separates the probe test fixtures and the array of fabric samples from the force sensors in a parallel dynamic mechanical analyzer.

FIG. 4, which illustrates the use of two flexure strips 150 to align the probes 104 with the samples 230, shows a cross-sectional view of one of the isolation block modules 124 as seen through a cutting plane containing centerlines of the apertures 122 shown in FIG. 2. The flexure strips 150 are sandwiched between generally planar surfaces of upper 152 and intermediate 154 segments of the isolation block module 124 and between generally planar surfaces of the intermediate 154 and lower 156 segments of the isolation module 124. The two flexure strips 150 shown in FIG. 4 comprise relatively thin (from about 10 $\mu$m to about 100 $\mu$m) rectangular membranes having spaced-apart holes that are substantially aligned with each composite shaft 120 within the apertures 122 of the isolation block modules 124.

As shown in FIG. 4, the composite shaft 120 is comprised of a rigid, substantially cylindrical core 158 and a thermally insulating outer sheathing having upper 160, intermediate 162, and lower 164 sections that are threaded onto the core 158. When installed in the apertures 122, the abutting ends of the upper 160 and intermediate 162 sections of the sheathing and the intermediate 162 and lower 164 sections of the sheathing lie in planes containing the two flexure strips 150. Since the diameters of the core 158 and the holes in the flexure strips 150 are about the same, the periphery of the holes are clamped between the abutting ends of the upper 160, intermediate 162, and lower sections of the sheathing. The flexure strips 150 are also clamped along the periphery of each aperture 122, adjacent interfaces between the upper 152, intermediate 154, and lower segments 156 of the isolation block module 124. The resulting clamped membranes or diaphragms 166, which span annular gaps 168 between the shafts 120 and the isolating block module 124, support and align the probes 104.

The geometry of the diaphragms 166 makes each of the flexure strips 150 compliant for displacements normal 114 to the surface supporting or containing the array 230, but mechanically stiff for displacements parallel to the array 230. The use of two flexure strips 150 also makes each combination of shaft 120 and diaphragms 166 mechanically stiff for angular displacements away from the direction normal 114 to the surface of the array 230. Moreover, through proper selection of materials and dimensions, the flexure strips 150 exhibit effective spring constants—for displacements normal 114 to the array 230—substantially less than effective constants of the sensors 106. In this way, the flexure strips 150 ordinarily exert minimal influence on the measured responses to protrusions, unless they are used to "pre-load" the sensors 106 as discussed below. Useful materials for the flexure strips 150 include metallic and polymeric films. For example, one particularly useful flexure strip material is polyimide film, which is available from DuPont under the trade name KAPTON in thickness ranging from about from about thirteen $\mu$m to about one hundred twenty five $\mu$m. Other useful flexure materials include stainless steel foil, diaphrams (in general) and corrugated bronze, for example, the flexure may be mechanically machined stainless steel. Since the effective spring constants of the diaphragms 166 and typical sensors 106 are temperature-dependent, the use of thermally insulating sheathing 160, 162, 164 on the shafts 120 permits the PDMA 100 to vary the temperature of the arrays 230 without significantly affecting the measured response.

Figure 5:
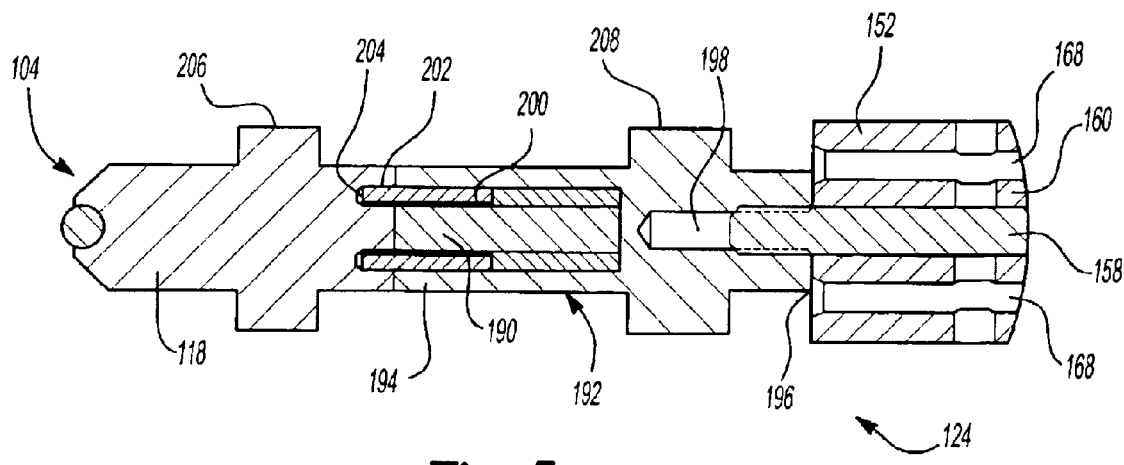
FIG. 5 shows a close-up cross sectional view of the probe shown in FIG. 4, and illustrates the use of a permanent magnet to attach the test fixture to the threaded cylindrical core of the composite shaft.

For the high throughput fabric handle screening, it is preferred that the PDMA 100 employs a probe 104 having a blunt end (not shown) for protruding the array 230. Alternatively, the probe 104 can be equipped with a blunt end test fixture 118 for protruding the array 230. The PDMA 100 may provide a mechanism for removing and securely attaching the test fixtures 118. Suitable attachment mechanisms include mechanical and electromagnetic couplings, as well as devices employing permanent magnets. FIG. 5 shows a close-up cross sectional view of the probe 104 shown in FIG. 4, and illustrates the use of a permanent magnet 190 to attach the test fixture 118 to the threaded core 158 of the composite shaft 120. As shown in FIG. 5, the probe 104 includes a base 192 having first 194 and second ends 196 that adjoin, respectively, the test fixture 118 and the upper section 160 of the thermally insulating outer sheathing. A substantially cylindrical bore 198 extends partway into the base 192 and is sized and threaded to connect the core 158 of the shaft 120 to the second end 196 of the base 192. The test fixture 118 is removably attached to the first end 194 of the base 192 by magnetic flux originating from the permanent magnet 190 that is embedded in the base 192 of the probe 104. A tubular magnetic shield 200, which typically has a lower modulus than either the probe base 192 or the permanent magnet 190, is wedged into an annular space between the probe base 192 and the permanent magnet 190. The shield 200, which helps secure the magnet 190 within the probe base 192, extends outward from the first end 194 of the base 192 and mates with a substantially circular slot 202 formed in the test fixture 104. The slot 202 is sized to receive the tubular shield 200 with minimal interference, and the shield 200 has a tapered end 204 that helps guide it into the slot 202 during attachment of the test fixture 118 to the probe base 192. In the embodiment shown in FIG. 5, the test fixture 118 and the test fixture 118 and the probe base 192 include flanges 206, 208 for accessing them during removal or attachment.

As can be seen in FIG. 5, the test fixture 118, the base 192, and the shield 200 enclose the permanent magnet 190, which helps minimize stray magnetic flux that may influence sample measurements of nearby probes 104. Generally, the probe 104 components are made from materials having a high magnetic permeability—a relative permeability substantially greater than unity—to ensure effective magnetic shielding. Suitable materials include nickel-iron alloys containing copper, molybdenum, or chromium and mixtures thereof. A particularly useful shielding material is available under the trade name HI-PERM 49 from Carpenter Technology. Other useful shielding materials include cold-rolled steel that has been chrome-plated to resist corrosion. The permanent magnet 190 should be fabricated from a material that provides sufficient force to secure the test fixture 118 to the probe base 192 during screening. Useful permanent magnets 190 include samarium cobalt magnets, ceramic ferrite magnets, aluminum-nickel-cobalt magnets, and neodymium-iron-boron magnets.

Figure 6:
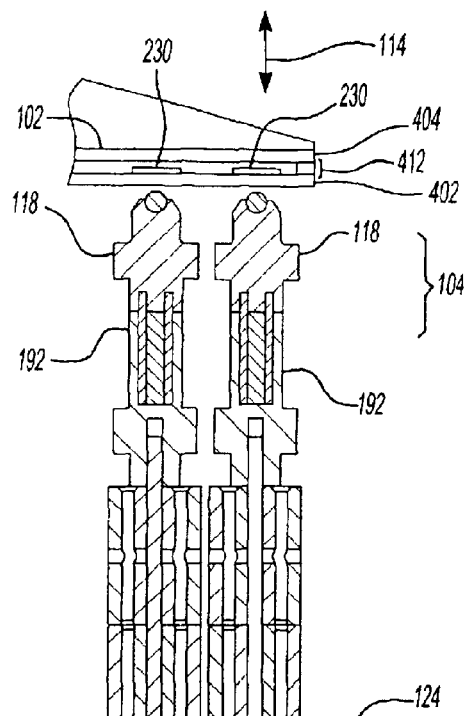
FIG. 6 shows a cross sectional view of two adjacent isolation block modules, and illustrates interactions of probes and force sensors in a parallel dynamic mechanical analyzer.
Figure 6:
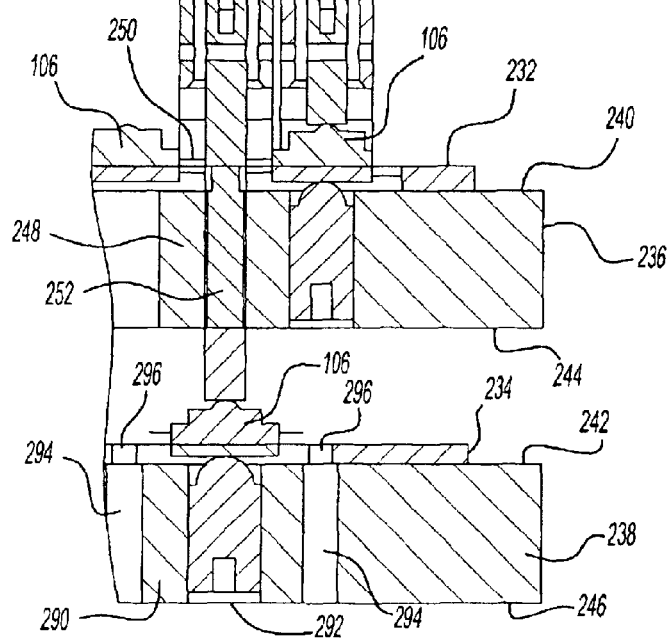

FIG. 6 illustrates interactions of the probes 104, the sensors 106, and the array of fabric samples 230. FIG. 6 shows a cross sectional view of the PDMA 100 of FIG. 2 taken from a plane that cuts through the two isolation block modules 124 and contains centerlines of two adjacent probes 104. During screening, each test fixture 118 portion of the probes 104 interacts with an individual array sample 230, which is positioned at a specific location 414 of the sample holder 102 over an opening 407. Movement of the sample holder 102 in a direction normal 114 to the surface of the array 230 results in forces that are transmitted to the sensors 106 via each probe test fixture 118, probe base 192, and composite shaft 120. Each composite shaft 120, which includes a rigid core 158 and thermally insulating outer sheathing 160, 162, 164, contacts the force sensor 106 directly or indirectly as discussed below.

The relatively large footprint of each sensor 106 shown in FIG. 6 makes it impracticable to mount all of the sensors 106 on a single plane while maintaining 9 mm spacing between centers 126 of adjacent sensors 106. Of course, using sensors with smaller footprints may allow for mounting in a single plane. To provide 9 mm spacing, the PDMA 100 employs sensors 106 mounted on first 232 and second 234 sensor boards, which rest on upper 236 and lower 238 rigid support plates, respectively. Both support plates 236, 238 include holes that extend from top surfaces 240, 242 of the plates 236, 238 to bottom surfaces 244, 246 of the plates 236, 238. The holes are arrayed on 9 mm centers, and are either threaded or non-threaded. Non-threaded holes 248 in the upper support plate 236 are substantially aligned with through-holes 250 in the first sensor board 232. The non-threaded holes 248 and the through-holes 250 are sized to provide passageways for rods 252 that transmit forces from the composite shafts 120 to sensors 106 mounted on the second (lower) sensor board 234. The PDMA 100 thus maintains the most preferred spacing by distributing the force sensors 106 among two boards 232, 234—thereby doubling the surface area available to mount the force sensors 106—and by arranging the sensors 106 so their centers 126 are 9 mm apart when projected on the surface of the array 230. When using smaller sensors or when 9 mm spacing is not desired, the PDMA may dispense with one of the two sensor boards. As many sensor boards as is practical for a particular embodiment may be employed.

Figure 7:
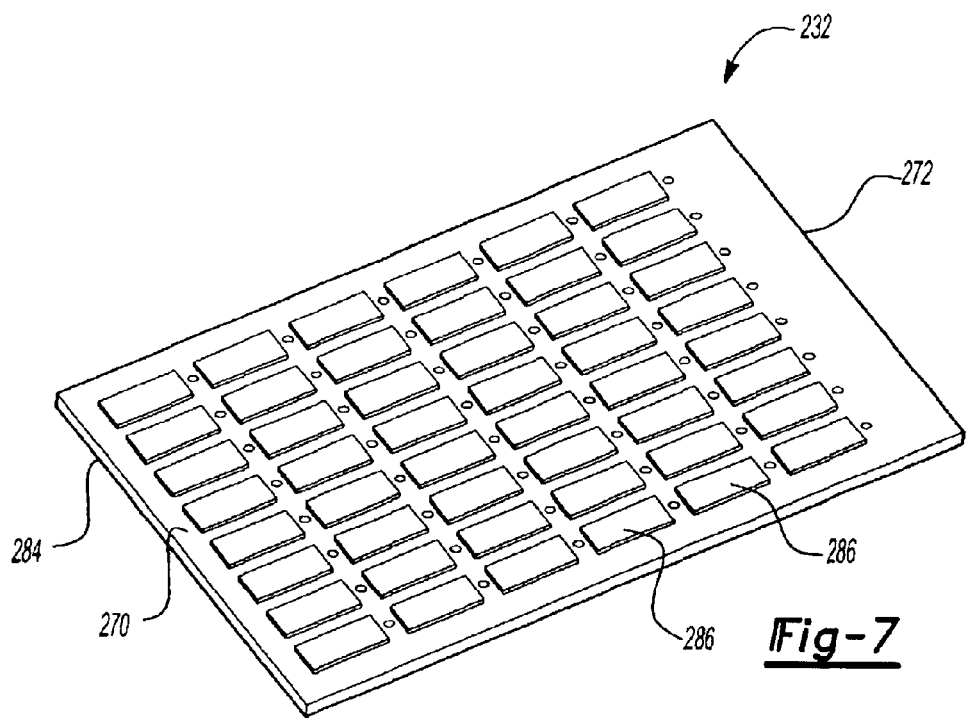
FIG. 7 shows a perspective bottom view of one of the sensor boards in a parallel dynamic mechanical analyzer.
Figure 8:
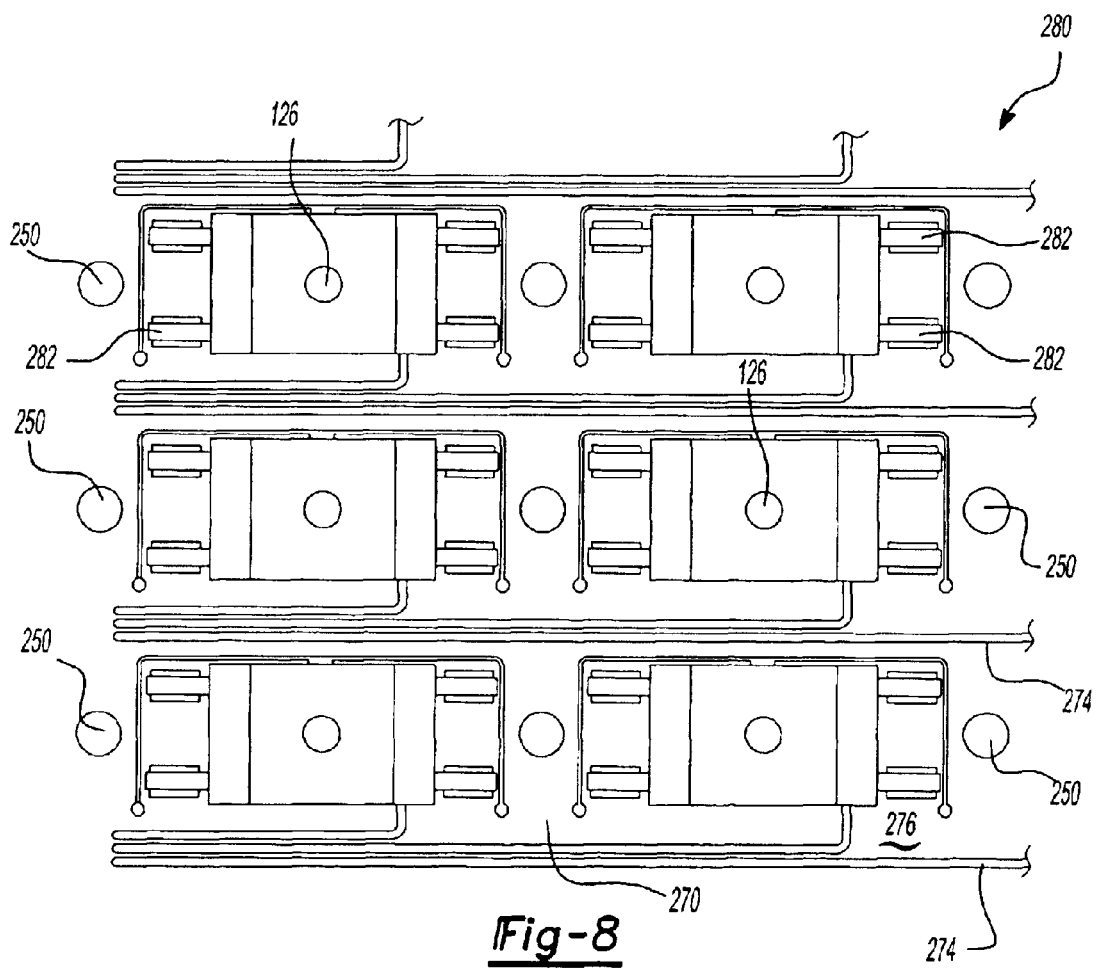
FIG. 8 shows a top view of a portion of one of the sensor boards in a parallel dynamic mechanical analyzer.

FIG. 7 and FIG. 8 provide further details of the sensors 106 and sensor boards 232, 234, showing respectively, a bottom perspective view and a close-up top view of the first sensor board 232. The first 232 and second 234 sensor boards generally comprise a flexible multi-layer dielectric sheet 270 (e.g., polyimide) and a rigid frame 272 (e.g., FR-4 epoxy glass laminate) that is bonded to the periphery of the dielectric sheet 270. Electrically conductive traces 274 are embedded on top 276 or bottom surfaces of the dielectric sheet 270, or between layers of the flexible sheet 270, forming a double-sided flex circuit 280. Each sensor 106 is mounted on the top surface 276 of the flex circuit 280, and leads 282 on the sensors 106 are connected to conductive traces 274 that terminate at a standard card edge connector 284. Conventional ribbon cables can be used to link the card-edge connector 284 with peripheral recording and control devices (not shown) allowing communication between the sensors 106 and the peripheral devices.

As shown in FIG. 7, the first 232 and second 234 sensor boards include generally planar stiffeners 286 (e.g., FR-4 epoxy glass laminates) attached to the bottom surface 278 of the sensor boards 232, 234 directly below the sensors 106. Each of the stiffeners 286 has about the same footprint as the sensors 106, and helps distribute loads on, and prevent bending of, the sensors 106. Note however, the stiffeners 286 do not prevent movement of the sensors 106 in a direction normal 114 to the array 230 since the sensors 106 are mounted on the flexible dielectric sheet 270. Although other embodiments can use rigidly-mounted sensors, the PDMA 100 shown in FIG. 2 uses sensors 106 mounted on the flex circuit 280 to allow "pre-loading" of the sensors 106 as discussed below. Pre-loading may of course be performed by other methods, which those of skill in the art will appreciate from a review of this specification. Furthermore, a detailed discussion of "pre-loading" is set forth in the commonly owned and co-pending U.S. patent application Ser. No. 09/580,024 titled "Instrument for High Throughput Measurement of Material Physical Properties and Method of Using Same," filed on May 26, 2000, which has been incorporated by reference.

The first sensor board 232 shown in FIG. 8 also includes a plurality of through-holes 250 that are located between the sensors 106. Following assembly of the PDMA 100, the through-holes 250 are substantially aligned with unthreaded holes 248 in the upper support plate 236 (FIG. 6). As noted above, the unthreaded holes 248 in the upper support plate 236 provide passageways for rods 252 that transmit forces from the composite shafts 120 to sensors 106 mounted on the second (lower) sensor board 234. Thus, the centers 126 of the sensors 106 and the through-holes 250 of the first sensor board 232 are arrayed on 9 mm centers.

Referring to FIGS. 6–8, threaded holes 248, 290 in the upper 236 and lower 238 support plates are sized to receive set-screws 292 that the PDMA 100 can use to pre-load each of the sensors 106 mounted on either the first 232 or second 234 sensor boards. As noted in the description of FIG. 4, the flexure strips 150 used to align the probes 104, are compliant for displacements normal 114 to the plane containing the array 230, but are mechanically stiff for displacements in other directions. Moreover, the effective spring constants of the flexure strips 150 are substantially less than the spring constants of the sensors 106 so that the flexure strips 150 ordinarily exert minimal influence on the measured responses of the array 230 to protrusions. However, since the sensors 106 are mounted on the flex circuit 280, the set-screws 292 can apply a force to the stiffeners 286 and the sensors 106 in absence of a force on the test fixture 118. A force recorded by the sensors 106 will therefore be the sum of the force acting on the test fixture 118 and the pre-load force. Since many commercial force sensors can detect only tensile or compressive loads, pre-loading permits a compressive sensor to detect small tensile loads, or a tensile sensor to record small compressive loads, expanding the capabilities of the PDMA 100. Note that the lower support plate 238 and the second sensor board 234 both include unthreaded holes 294, 296 that provide access to the set-screws 292 in the upper support plate 236.

The PDMA 100 can use a wide variety of sensors 106, including miniature force sensors. Most of the sensors 106 incorporate signal conditioning electronics. Suitable force sensors include piezoresistive micromachined silicon strain gauges that form a leg of a conventional Wheatstone bridge circuit. A useful low-compliant force sensor is available from Honeywell under the trade name FSL05N2C. The Honeywell force sensor has a 500-g range (4.9 N full scale), which is suitable for most of the screening methods described in subsequent sections. As noted earlier, many force sensors can tolerate only modest variation in temperature without compromising accuracy and precision. The use of a composite shaft 120 having an insulating sheathing 160, 162, 164 (FIG. 4) permits substantial temperature variation of the array 230 without significantly affecting the temperature and accuracy of the sensors 106.

In an alternative embodiment, force sensors are incorporated into the flexure strips 150 by placing strain gages on the diaphragms 166 (FIG. 4). Strain resulting from the application of a known force—typically a deadweight load applied to the rigid shaft 120—is recorded and used to develop a calibration curve for the force sensor. The principal disadvantage of this approach is the extensive signal conditioning requirements associated with strain gage measurements.

Referring again to FIG. 2 and FIG. 4, the PDMA 100 may include an environmental chamber (not shown) that encloses the sample holder 102, the probes 104, and the upper 152 or intermediate 154 segments of the isolation block modules 124 that control the environment (e.g., temperature, humidity, etc.) of the samples 230. The chamber may be filled with a gas of known composition to study its influence on the fabric handle of the samples 230. Generally, the annular gap 168 between the composite shafts 120 and the cylindrical apertures 122 is minimized to limit the flow of gas out of the isolation block modules 124. In addition, the flexures 150 in the annular gaps 168 restrict gas efflux from the isolation block modules 124.

Alternatively, the environmental chamber may comprise a substantially gas-tight enclosure that surrounds the sample holder 102, the probes 104, the isolation block modules 124, and the sensors 106. The enclosure may be further separated into two compartments—one that encloses the sample holder 102 and the samples 230, and one that encloses the sensors 106 and the isolation block modules 124. The latter embodiment allows blanketing the sample holder 102 and the samples 230 with a first gas that is different than a second gas blanketing the sensors 106. In this way, the PDMA can vary the environment of the samples 230 independently of the sensors 106, while maintaining the sensors 106 at conditions different than or the same as the laboratory environment.

The environmental chamber may include devices for regulating and/or monitoring the temperature of the samples 230. Useful devices include one or more heating or cooling elements placed within a gas stream that feeds the environmental chamber containing the array 230. Other useful devices include an array of radiant heaters positioned adjacent to the samples 230. Alternatively, the PDMA 100 may include resistance heaters or thermoelectric devices that are attached to the sample holder 102, which heat or cool individual or groups of samples in the array 230. The PDMA 100 may also include devices such as thermocouples, thermistors, or resistive thermal devices (RTD) for monitoring the temperature of individual samples 230. In some embodiments, the PDMA 100 includes a temperature controller, such as a data acquisition board, for subjecting the array 230 to a desired temperature-time profile. The temperature controller automatically adjusts the power supplied to the heating and cooling devices in response to signals received from the temperature monitoring devices. Typically, software running on an external computer communicates and coordinates functions of the temperature controller and the temperature monitoring devices.

Parallel Dynamic Mechanical Analyzer Control and Data Acquisition

Figure 9:
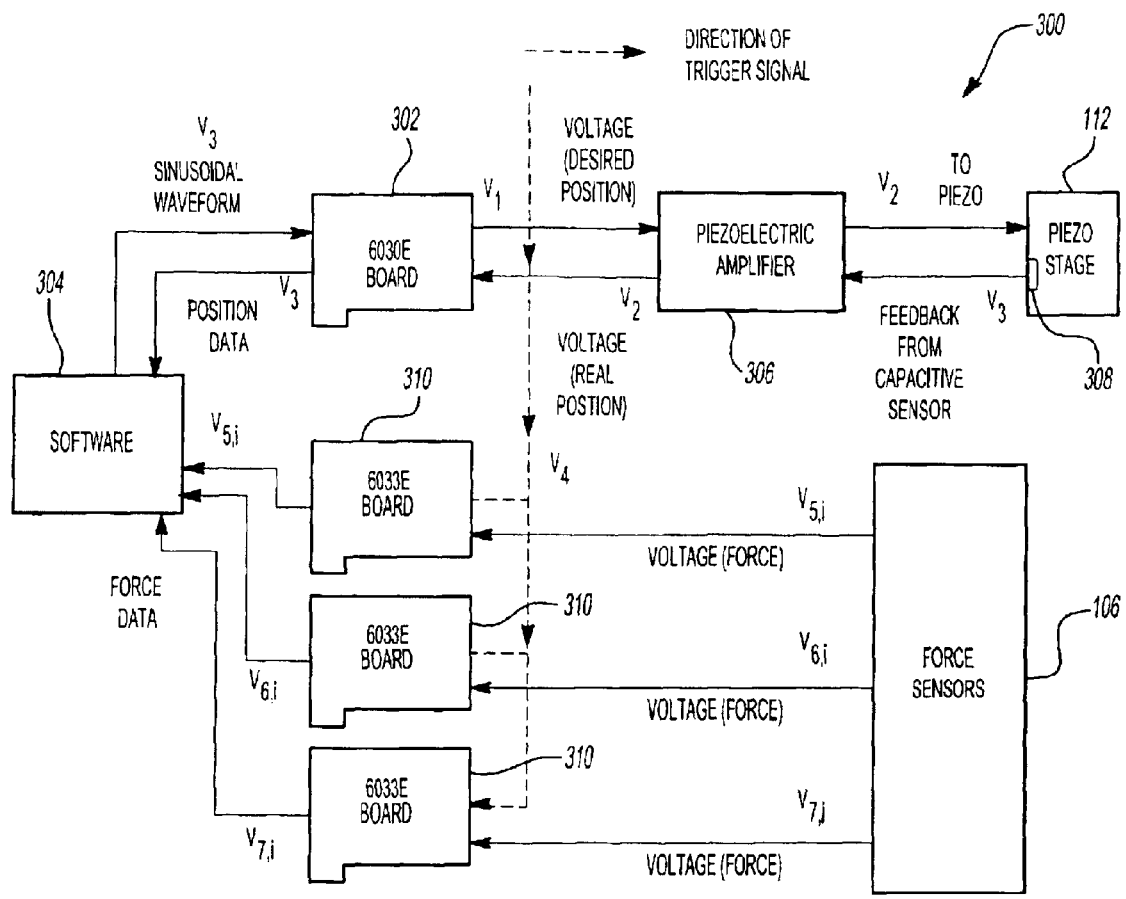
FIG. 9 is a flow chart for the data acquisition control for a parallel dynamic mechanical analyzer.

FIG. 9 shows schematically a system 300 for data acquisition and control of the PDMA. As noted in the discussion of FIG. 2, the PDMA 100 includes first 110 and second 112 translation actuators for displacing the array 230 (FIG. 6) in a direction normal 114 to the probes 104. The first translation actuator 110 provides relatively coarse displacement of the sample holder 102; it positions the samples 230 near the probe 104 test fixtures 118, and can be regulated using a DC motor controller (not shown). The second translation actuator 112 provides relatively fine displacement of the sample holder 102 and is responsible for carrying out protrusions of the individual samples 230.

The second translation actuator 112 shown in FIG. 9 comprises a piezoelectric translation stage. A primary data acquisition board 302 (e.g., National Instruments 6030E), which is located in an external computer 304, controls the operation of the second translation actuator 112. The primary board 302 generates a voltage, $V_1$, which is proportional to the desired displacement of the actuator 112 (and sample holder 102). This voltage is fed to a piezoelectric amplifier 306 that monitors the position of the actuator 112 via a capacitive position sensor 308. In response to $V_1$, the piezoelectric amplifier 306 varies the charge, $V_2$, which it supplies to the actuator 112 to move the sample holder 102 to its desired position. The position sensor 308 generates a voltage, $V_3$, which is read by the amplifier 306 and indicates the actual position of the second translation actuator 112.

As shown in FIG. 9, the primary data acquisition board 302 and the external computer 304, respectively, read and record $V_3$. In response to the value of $V_3$, the primary board 302 updates $V_1$ as necessary and generates a timing pulse, which triggers acquisition of $V_3$ from the position sensor 308, thereby synchronizing signals $V_1$ and $V_3$. The acquisition of $V_3$ also generates a second timing pulse, $V_4$, which triggers acquisition of voltages $V_{5,i}$, $V_{6,i}$, and $V_{7,i}$, from the sensors 106. Secondary data acquisition boards 310 acquire $V_{5,i}$, $V_{6,i}$, and $V_{7,i}$, where subscript refers to a particular data line (channel) of the data acquisition board 310. Thus, measurements of the response of the array 230 to protrusions are synchronized with the motion of the second translation actuator 112 (and sample holder 102), and the measurement of the actuator 112 position. Although the system 300 shown in FIG. 8 uses three secondary data acquisition boards 310 having 32 channels each, the number of boards 310 will depend on the number of available data channels and sensors 106. Alternatively, the PDMA may use a single data acquisition board to control the actuator 112 position and to acquire sensor 106 data, assuming the board has a sufficient number of data channels and output signals.

Software running on the computer 304 coordinates the activities of the boards 302, 310 and allows the user to specify screen parameters including positions of the first 110 and second 112 translation actuators at any given time, the number of samples 230, and so on.

General Methodology

The methodology for high throughput fabric handle screening used in this experiment generally includes the following steps: (1) providing a plurality of samples of non-woven materials; (2) aggregating the materials in a binder; (3) placing the samples on a sample holder having a plurality of openings with smooth edges; (4) protruding the samples; (5) measuring the response of each sample; (6) comparing the samples relating to each other; (7) identifying the samples that meet predetermined criteria and/or ranking the samples based upon their individual performance; and (8) preparing bulk scale quantities of a material or materials based upon the results of this high throughput fabric handle screening.

Method of Screening Fabric Handle Using the Parallel Dynamic Mechanical Analyzer Referring to FIG. 3, the method of screening fabric handle using the PDMA 100 begins with placing the array of fabric samples 230 between the first plate 402 and the second plate 404 of the sample holder 102 with the individual samples 230 confined to specific locations 414 on the sample holder 102. Thereafter, the samples 230 in the sample holder 102 are translated in a direction normal to the ends 116 of the probes 104. Alternatively, as discussed above, the translation can be achieved by the probes 104 in a direction normal to the sample holder 102 or both by the probes 104 and the sample holder 102 in a direction normal to both. The translation is preferred to be conducted at a constant speed controlled by the system 300. It is also preferred that the speed is less than 10 mm per second but greater than about 1 mm, but more preferably about 5 mm per second. As the samples 230 continue to translate in the direction normal to the ends 116 of the probes 104, they first contact the blunt ends of the probes 104 through the through-holes 406 of the first plate 402 and then begin to fold and are eventually, and preferably completely, forced through the openings 407 of the second plate 404. This typically requires, but is not limited to, a translation of at least about 15 to 20 mm. The translation from the point of first contact between the blunt ends of the probes 104 and the samples 230 should be a distance at least equal to, and preferably greater than, the radius of the samples 230. During the protrusions by the probe 104, each sample 230 is preferably first contacted by the probe 104 at its center point and then becomes folded, sheared, bent, compressed, elongated, and rubbed against the interior wall of the opening 407. The force sensors register all the forces transmitted through the probe 104 and the information is transferred to the system 300. The output is a trace of force versus position of the sample holder 102 providing a load-displacement curve as shown in FIG. 1

In a preferred embodiment, the probes 104 have about the same lateral spacing as the tunnels 410 and/or the openings 407 so that there is a one-to-one correspondence between the individual probes 104 and the samples in the array 230. In addition, since the array 230 and the ends of the probes 104 also define two generally planar surfaces, the system can protrude all of the array samples 230 simultaneously by displacing the array 230 (sample holder 102) and/or the probes 104 in a direction normal to the two surfaces. If adapted to protrude all of the array samples 230 simultaneously, the system may include a rectilinear translation stage that is attached to the sample holder 102 or the probes 104.

In other embodiments, the system may protrude individual or groups of array samples 230 in a rapid serial fashion. In these embodiments, the system may include a translation mechanism capable of three-dimensional motion, which is attached to a single probe 104, to a group of probes 104, or to the sample holder 102.

The Automated Rapid Serial System

Figure 10:
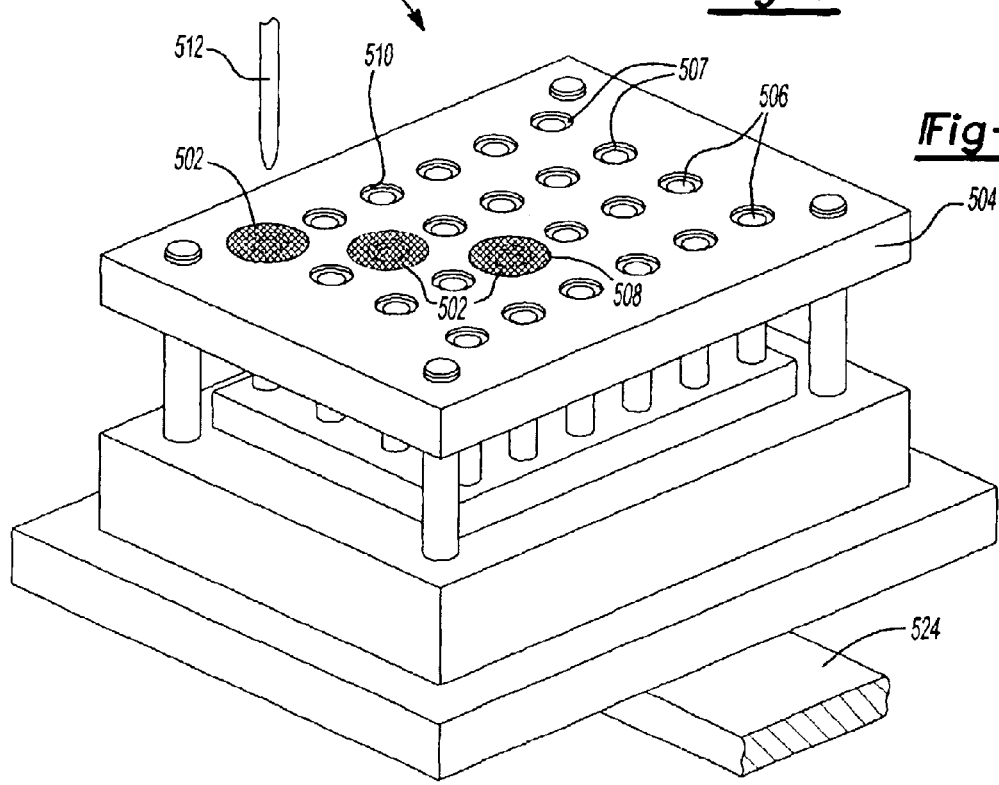
FIG. 10 shows a perspective view of one embodiment of an automated rapid serial system that can be used for high throughput fabric handle screening.

FIG. 10 shows a perspective view of another instrument suitable for screening, and specifically, an automated rapid serial system (ARSS) 500 that can be used to conduct high throughput fabric handle screening of an array of fabric samples by measuring responses of the array samples to protrusions. The ARSS 500 can be configured for use with parallel, serial or serial-parallel protocols. In a most preferred embodiment, the ARSS 500 can be configured for use in a rapid serial fashion with a high sample screening throughput. Detailed description of the ARSS 500 is described in commonly owned and co-pending U.S. patent application Ser. No. 09/939,252 titled "High Throughput Mechanical Rapid Serial Property Testing of Material Libraries," (P. Mansky) filed on Aug. 24, 2001, which is herein incorporated by reference. Generally, ARSS 500 includes a variety of robotic instruments for automatically or programmably providing predetermined motions for protruding an array of fabric samples 502 according to a predetermined protocol. ARSS 500 may be adapted or augmented to include a variety of hardware, software or both to assist it in determining the fabric hand of the array members. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652 or BioDot Microdrop Model 3000).

Figure 11:
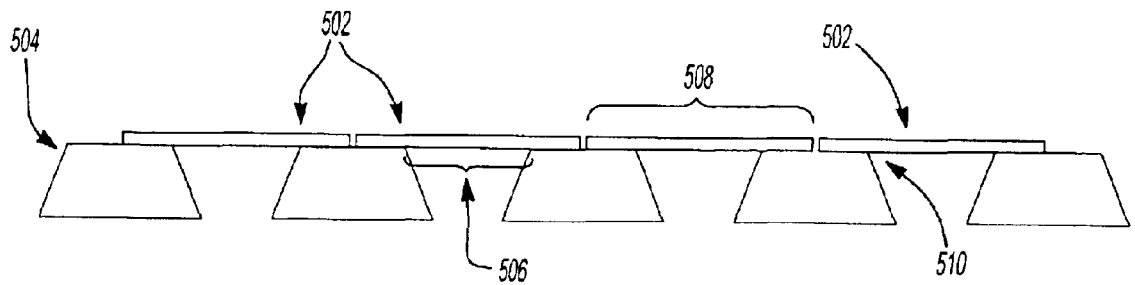
FIG. 11 shows one preferred embodiment of a sample holder that can be used in the automated rapid serial system.

Referring to FIG. 10 and FIG. 11, the ARSS 500 includes a sample holder 504 having a plurality of openings 506. The array of fabric samples 502 is preferably confined to specific locations 508 located on the sample holder 504 with one to one correspondence between the specific locations 508 and the openings 506, and that the array samples 502 do not overlap each other but include and extend beyond the regions defined by the diameter of the openings 506. It is also preferred that each opening 506 is surrounded by an indentation 507 in the sample holder 504 that restricts any horizontal movement of its respective sample 502. This indentation is similar to the indentation in the second plate 404 shown in FIG. 3C for the PDMA 100 instrument.

It is further preferred that each sample 502 is at least about 2 times larger than the diameter of the opening 506, more preferred at least about 5 times larger than the diameter of the opening 506, and most preferred about 10 times larger than the diameter of the opening 506. The particular sample holder 504 shown in FIG. 10 and FIG. 11 contains a 4-by-6 rectangular array of fabric samples 502 located on 18 mm centers. However, the sample holder 504 can be designed to contain any number of samples in an array. For example, the sample holder 504 can be designed to contain 4 or more, 8 or more, 16 or more, or 48 or more samples in an array.

Those of skill in the art will appreciate that this is simply a matter of design choice and the invention herein is not limited to the specific embodiments described in detail. The size and shape of the openings 506 can affect the fabric handle measurements and are taken into consideration in measuring the fabric handle of the array samples 502. For instance, the opening 506 need to be large enough for the sample 502 to collapse upon itself naturally but still has a portion of itself in physical contact with the walls of the opening 506 during the protrusions. Referring to FIG. 11, one preferred leading edge 510 to the opening 506 allows for a smooth transition for the sample 502 to transfer from a flat state to the bent and folded state which occurs during the protrusions. Thus, it is preferred that the opening 506 is constructed out of a smooth material or coated with a smooth material (e.g., a plastic layer, a coating, or the like). Although the openings 506 can be any shape and/or size, it is preferred that they 506 are funnel-shaped or otherwise a rounded or a tapered periphery with a diameter at the top of each funnel that is twice of the bottom diameter, and with the height of the sloped section at least equal to the height of the straight section. The alternative embodiments of openings shown in FIGS. 3C-J are also applicable for the ARSS 500. Alternatively, the sample holder 504 can have the same specifications as the sample holder 102 described above for the PDMA 100.

The ARSS 500 also includes a probe 512 (or other similarly functioned device) having a blunt end for protruding the array 502. Alternatively, the probe 512 can be equipped with a blunt end test fixture 118 for protruding the array 502. The ARSS 500 can generally include as many probes 512 as desired, for example there may be as many as probes 512 as there are samples in the array 502 and in a preferred embodiment, the probes 512 have about the same lateral spacing as the openings 506 so that one probe 512 is associated with one opening 506 or sample 502. Alternatively, the ARSS may employ fewer probes 512 than samples in the array 502, so that a group of probes 512 protrudes multiple samples 502, or there may be more probes 512 than samples in the array 502. Alternatively, there may be only one probe 512 and the ARSS 500 includes a translation mechanism capable of three-dimensional motion, which is attached to the single probe 512 or to the sample holder 504 to allow high throughput screening in a rapid serial fashion.

The ARSS 500 includes actuator(s) for moving the probe (s) 512 and the samples 502 in relation to each other. In one preferred embodiment, the actuator is attached to the probe 512 and the samples 502 remain stationary. In another preferred embodiment, the actuator is attached to the sample holder 504 and the probe 512 remains stationary. In yet another preferred embodiment, both the probe 512 and the sample holder 504 have actuators attached allowing both of them to translate.

Figure 12:
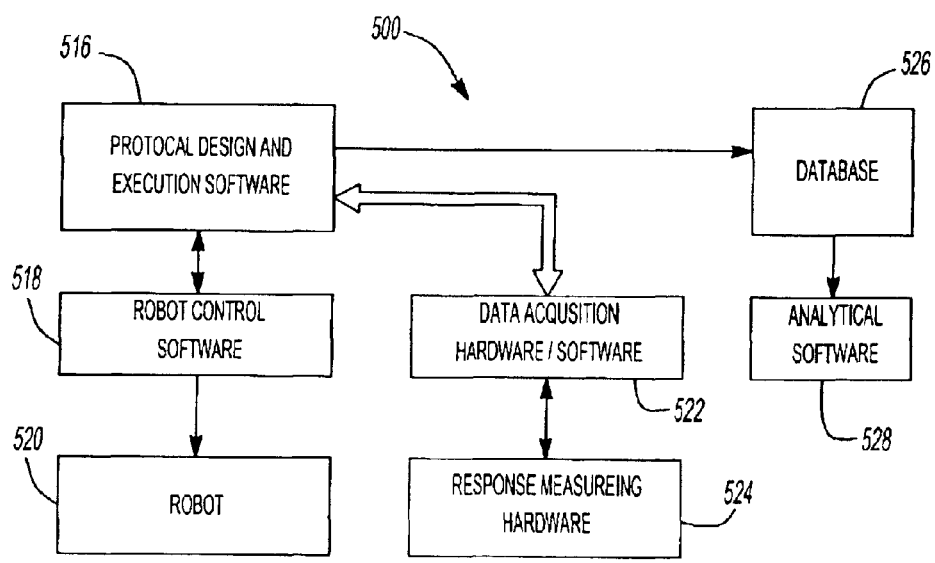
FIG. 12 is a flow schematic diagram of the automated rapid serial system that can be used for high throughput fabric handle screening.

Referring to FIG. 12, there is a flow schematic diagram of the ARSS 500 for rapid determination of the fabric hand of the array 502. Generally, the ARSS 500 includes a suitable protocol design and execution software 516 that can be programmed with information such as location information or other information related to the samples 502 positioned with respect to a sample holder 504. The protocol design and execution software 516 is typically in communication with robot control software 518 for controlling a robot 520 or other automated system. The protocol design and execution software 516 is also in communication with data acquisition hardware/software 522 for collecting data from response measuring hardware 524. Preferably, the robot control software 518 commands the robot 520 having the probe 512 to protrude the samples 502 through the openings 506. At substantially the same time, the response measuring hardware 524 (e.g., sensors, transducers, load cells and the like) monitors the responses of the samples 502 to the protrusions and provides data on the responses to the data acquisition hardware/software 522. Thereafter, the robot control software 518, the data acquisition hardware/software 522 or both transmit data to the protocol design and execution software 516 such that information about the samples 502 may be matched with the samples' 502 responses to the protrusions and transmitted at data to a database 526. Once the data is collected in the database 526, analytical software 528 may be used to analyze the data, and more specifically, to determine the mechanical properties associated with the fabric hand of the samples 502 or the data may be analyzed manually.

In a preferred embodiment, the ARSS 500 is employed in association with suitable software for combinatorial materials research, such as LIBRARY STUDIO™, by Symyx Technologies, Inc. (Santa Clara, Calif.); IMPRESSIONIST™, by Symyx Technologies, Inc. (Santa Clara, Calif.); EPOCH™, by Symyx Technologies, Inc. (Santa Clara, Calif.); POLYVIEW™, by Symyx Technologies, Inc. (Santa Clara, Calif.) or a combination thereof. The skilled artisan will appreciate that the above-listed software can be adapted for use in the present invention, taking into account the disclosures set forth in commonly-owned and copending U.S. patent application Ser. No. 09/174,856 filed on Oct. 19, 1998, U.S. patent application Ser. No. 09/305,830 filed on May 5, 1999 and WO 00/67086, U.S. patent application Ser. No. 09/420,334 filed on Oct. 18, 1999, U.S. application Ser. No. 09/550,549 filed on Apr. 14, 2000, each of which is hereby incorporated by reference. Additionally, the system may also use a database system developed by Symyx Technologies, Inc. to store and retrieve data with the overlays such as those disclosed in commonly-owned and copending U.S. patent application Ser. No. 09/755,623 filed on Jan. 5, 2001, which is hereby incorporated by reference for all purposes. The software preferably provides graphical user interfaces to permit users to design arrays of fabric samples by permitting the input of data concerning the precise location on the sample holder 506 of each sample in the array (i.e., the address of each sample). Upon entry, the software will execute commands to control movement of the robot, for controlling activity at such individual address. Data obtained from the analysis can be compiled and analyzed.

Optionally, the ARSS 500 further includes an environmental chamber for controlling the environment (e.g., temperature, humidity, etc.) of the array. An example of a suitable environmental chamber is a thermal jacket for heating and cooling the array 502 as desired (e.g., preferably between −100° C. and 200° C.). One preferred thermal jacket includes passages for receiving a heated or cooled fluid such as liquid nitrogen, water, steam or other suitable fluid from a fluid supply. The fluid from the fluid supply may be pumped to the thermal jacket with a pump that is controlled by a controller.

Method of Screening Fabric Handle Using the Automated Rapid Serial System

Referring to FIGS. 10–12, the method of screening fabric handle using the ARSS 500 begins with placing the array of fabric samples 502 in specific locations 508 on the sample holder 504. Thereafter, the robot 520, preferably controlled by the robot control software 518, translates the probe 512 into contact with each sample in the array 502. Alternatively, as discussed above, the translation can be achieved by the sample holder 504 or by both the probe 512 and the sample holder 504. The translation is preferred to be conducted at a constant speed controlled by the ARSS 500. It is also preferred that the speed is less than 10 mm per second but greater than about 1 mm, but more preferably about 5 mm per second. After initial contact between the probe 512 and the sample 502, continued translation causes the sample 502 to fold and is eventually forced through the opening 506 as the probe 512 protrude the sample 502. The protrusion typically requires, but is not limited to, a translation of at least about 15 to 20 mm. The translation from the point of first contact between the blunt end of the probe 512 and the sample 502 should be a distance at least equal to, and preferably greater than, the radius of the sample 502. During the protrusions by the probe 512, each sample 502 is preferably first contacted by the probe 512 at its center point and then becomes folded, sheared, bent, compressed, elongated, and rubbed against the interior wall of the opening 506. The response measuring hardware 524 register all the forces transmitted through the probe 512 and the information is transfer to the data acquisition hardware/software 522. Thereafter, the robot control software 518, the data acquisition hardware/software 522 or both transmit data to the protocol design and execution software 516 such that information about each sample in the array 502 may be matched with its responses to the protrusions and transmitted at data to a database 526. Once the data is collected in the database 526, analytical software 528 may be used to analyze the data, and more specifically, to determine the mechanical properties associated with the fabric hand of each sample in the array 502 or the data may be analyzed manually. Generally, the output is a load-displacement curve as shown in FIG. 1.

Interpretation of the Load-Displacement Curve

The load-displacement curve obtained during the high throughput fabric handle screening methods discussed above contains information about various mechanical properties associated with fabric handle such as bending modulus, shear stiffness, compression, friction, and extensibility. Due to the extreme complexities of the interactions of these mechanical properties throughout the duration of the screen, extraction of the various properties from the curve is extremely difficult. See Pan, Ning and Yen, K. C., "Physical Interpretations of Curves Obtained Through the Fabric Extraction Process for Handle Measurement," *Textile Res. J.* 65(5), 279–290 (1992). The maximum force reached during the protrusion is thus taken to be representative of the overall fabric handle, incorporating all of the various mechanical properties into one value.

Screening Throughput

The instruments described above in accordance with the present invention can analyze an array having 2 or more samples, and preferably, at least 8 samples to ensure adequate screening throughput. Those of skill in the art will appreciate that lower or higher throughput may serve the needs of a particular application of this invention. Thus, 4 or more, 8 or more, 16 or more, 24 or more, or 48 or more probes in parallel are within the scope of this invention. These probes may all be in the same test fixture or in multiple test fixtures.

As for screening throughput for parallel embodiments, up to 96 array samples may have their mechanical properties associated with fabric handle measured simultaneously in about 10 minutes or less, preferably about 5 minutes or less and even more preferably in about 1 minute or less. In some parallel embodiments, screening throughput of even about 30 seconds or less may be accomplished for an array of the sizes discussed herein, e.g., up to 96 samples in the array.

For the rapid serial or the hybrid parallel-serial embodiments, fabric handle of each sample in the array is detected at an average sample throughput of not more than about 2 minute per sample. As used in connection herewith, the term "average sample throughput" refers to the sample-number normalized total (cumulative) period of time required to detect the fabric handle of two or more fabric samples within an array. The total cumulative time period is delineated from the initiation of the screening process for the first fabric sample, to the detection of the fabric handle of the last fabric sample and includes any intervening between-sample pauses in the process. The sample throughput is preferably not more than about 30 seconds per sample, more preferably not more than about 20 seconds per sample, even more preferably not more than about 15 seconds per sample, and most preferably not more than about 10 seconds per sample.

It will be appreciated from the above that many alternative embodiments exist for high throughput fabric handle screening within the scope of the present invention. For example, instead of using probes, the PDMA 100 and the ARSS 500 can be configured to protrude the array samples by clamping, suctioning or pinching a portion (preferably the center portion) of each sample and pulling the sample through the opening. Accordingly, the methods and instruments discussed above are to be considered exemplary and nonlimiting as to the scope of the invention.

EXAMPLE

An example of the present invention is performed upon an airlaid non-woven fabric materials. The experiment begins with cutting an airlaid non-woven fabric material into a rectangle approximately 2"×1" in size and sandwiching between two pieces of polyester scrim to hold the fabric material together during the padding process. The fabric material is placed into a shallow container and soaked with 300 ml of binder solution (generally an emulsion). The binder solution is diluted down sufficiently so that the percent weight added on to the non-woven fabric material during this process is about 15%. The wet fabric material is passed between two rubber-coated rollers with a self-adjusting gap to squeeze out the excess liquid and ensure a uniform distribution of polymer solids throughout the fibers. The sample is dried at 110° C. for approximately 10 minutes, either with or without the scrim. Depending on the emulsion (i.e., is there cross-linker in the system), there is a curing step following the drying step at 130° C. for 5 minutes. Thereafter, the fabric material is cut to form 4 fabric samples with each sample being a 2 cm diameter circle. This process of preparing the fabric samples is repeated 6 times, each time with a different binder to yield an array of 24 fabric samples. The fabric samples are then arranged in a 4×6 array and centered over the funnel-shaped openings in the sample holder. For the 4×6 array, the outer lip of each of the funnel-shaped openings is 12 mm in diameter, and the inner opening is 6 mm in diameter. The centers of the openings are spaced 18 mm apart. After the array is placed onto the sample holder, they are then placed onto a cantilever-type load cell with a maximum allowable force of 50N. The output of the load cell is a voltage, but a calibration curve can be used to translate the voltage into a force (in this case, the relationship is F=30.96*V). Using the robotics-control software, the center of the first opening and the center of the last opening are identified. The fabric hand screening is run using Symyx' Impressionist™ and Epoch™ software. The probe is translated to a position slightly above the sample centered on the opening, and moved the probe downwards at a relatively slow speed (~5-10 mm/sec), and collects the response of the load cell as force is applied to the sample. This is repeated for each sample on the array. When the program is finished with its data collection, a suitable fitting routine goes back and fits each peak in the voltage versus time output, identifying such values as peak height and peak width. These parameters are saved to a database, from where they can be later retrieved along with the actual load-displacement curves.

The screening process takes approximately 5 seconds per sample allowing the entire array of 24 samples to be screened in less than 2 minutes. The peak height of each of the load-displacement curves is used to rank the fabric hand of the 6 different binders. The ranking of fabric hand using the above-described rapid serial technique yielded results matching human panel fabric handle screens as shown in Table 1. The fabric materials are correlated from soft to stiff with increasing peak height. For comparison by a human panel test, panelists are asked to rank the fabric samples in the array from 1 to 6 for softest to stiffest. The total points a sample received is divided by the number of panelists to obtain the ranking. In the human panel test, half of the participants rank the array samples in the same order as the rapid serial test and the other half have two array samples switched.

TABLE 1

| Sample Identification | Peak height | Force applied to sample | Ranking by Human Panel |
| --- | --- | --- | --- |
| A | 0.0552 | 1.71 N | 1 |
| B | 0.0761 | 2.36 N | 2 |
| C | 0.0786 | 2.43 N | 3.5 |
| D | 0.1059 | 3.28 N | 3.5 |
| E | 0.2604 | 8.06 N | 5 |
| F | 0.2631 | 8.15 N | 6 |

What is claimed is:

1. A method for screening fabric handle of an array of fabric samples, comprising:
   providing an array of at least four fabric samples upon at least one substrate;
   providing at least one probe;
   causing protrusions of each of said fabric samples through openings in said at least one substrate;
   wherein said protrusions are caused by contacting a said at least one probe with said fabric samples using an automated system that moves said at least one probe, said fabric samples, or both relative to each other in at least two orthogonal directions; and
   wherein said protrusions are caused at a throughput rate no greater than about two minutes per sample; and
   monitoring a response of each of said fabric samples to said protrusions for assisting in measuring relative fabric handle for each of said fabric samples.

2. The method of claim 1, wherein the method is capable of screening at least two of said fabric samples simultaneously.

3. The method of claim 1, wherein the method is capable screening at least twenty-four of said fabric samples simultaneously.

4. The method of claim 1, wherein average sample throughput is not more than about 20 seconds per said fabric sample.

5. The method of claim 1, wherein said array contain at least two different fabric materials.

6. The method of claim 1, wherein said fabric samples comprise of at least one material selected from the group consisting of woven materials, non-woven materials, knit materials, pile materials, blend materials, composite materials, and a combination thereof.

7. The method of claim 1, wherein at least one of said fabric samples has been subject to textile treatment selected from the group consisting of acrylic coating, airo finishing, bleaching, resin treatment, sanding, scenting, shearing, silver coating, wax coating, stonewashing, bonding, enzyme washing, flocking, glazing, mercerizing, milling, fulling, color treatment, texture treatment, bacterial resistant treatment, soil resistant treatment, oil repellent treatment, flame resistant treatment, pill resistant treatment, water resistant treatment, mildew resistant treatment, water repellant treatment, wrinkle resistant treatment, ultra violet resistant treatment, and a combination thereof.

8. The method of claim 1, wherein at least one of said fabric samples has been treated with an additive selected from the group consisting of binders, surfactants, fillers, reinforcements, flame retardants, colorants, environmental protectants, performance modifiers, control agents, plasticizers, cosolvents, accelerators, and a combination thereof.

9. The method of claim 1, wherein said protrusions are completed without piercing said fabric samples.

10. The method of claim 1, wherein said openings are shaped in a fashion that allows said fabric samples to fold naturally providing a smooth transition for said fabric samples to transfer from a flat state to a bent and folded state during said protrusions, and allows contact to exist between said fabric samples and said openings' interior walls during said protrusions.

11. The method of claim 1, wherein each of said openings is funnel-shaped having its top diameter that is about twice of its bottom diameter and its sloped section is about at least equal to height of its straight section.

12. The method of claim 1, wherein said openings are each individually surrounded by an indentation that restricts said fabric samples' horizontal movement.

13. The method of claim 1, wherein the diameter of said fabric samples is greater than about two times the diameter of said openings.

14. The method of claim 1, wherein the diameter of each of said fabric samples is less than about eighteen millimeters but is greater than about eight millimeters.

15. The method of claim 1, wherein said protrusions causes said fabric samples to fold and are eventually and completely forced through said openings.

16. The method of claim 1, wherein each of said protrusions is of a distance at least equal to the radius of said fabric samples.

17. The method of claim 1, wherein said array of fabric samples are placed onto a sample holder having said openings and said fabric samples are individually confined in specific locations, each of said specific locations includes and extends beyond a region defined by diameter of said openings, and said fabric samples do not overlap each other.

18. The method of claim 1, further comprised of regulating environmental conditions of said fabric samples by an environmental chamber.

19. The method of claim 1, wherein said protrusions are further caused by translating said fabric samples in a direction normal to an end of at least one probe at a constant speed less than about ten millimeters per second but greater than about one millimeter per second.

20. The method of claim 1, wherein said monitoring response of said fabric samples to said protrusions are performed by at least one sensor and a data logger for recording said response.

21. The method of claim 1, further comprised of conducting an analysis selected from the group consisting of relative comparison of the fabric handle of said fabric samples, quantitative measurement of the fabric handle of said fabric samples, and comparison of the fabric handle of said fabric samples with the fabric handle of fabric materials not included in said array.

22. The method of claim 1, wherein monitoring said response of said fabric samples to said protrusions includes measuring said force exerted on said at least one probe by said fabric samples as functions of displacement between said at least one probe and said fabric samples.

23. The method of claim 1, wherein monitoring said response of said fabric samples to said protrusions includes measuring said force exerted on said at least one probe by said fabric samples as functions of time.

24. The method of claim 1, wherein said protrusions are caused by having said array placed in a movable sample holder translating in a direction normal to blunt end of said at least one probe.

25. The method of claim 1, wherein said protrusions are caused by having a blunt end of said at least one probe translating in a direction normal to said array.

26. The method of claim 1, wherein said at least one probe is comprised of a test fixture with a blunt end for protruding said fabric samples.

27. A method for screening fabric handle of an array of fabric samples, comprising:

placing an array of fabric samples having at least eight different fabric samples into a sample holder having a first plate having a plurality of through-holes and a second plate having a plurality of openings that are aligned forming tunnels within said sample holder: and wherein said fabric samples do not overlap each other and are individually confined in specific locations that are between said first plate and said second plate, each of said specific locations includes and extends beyond a region defined by diameter of said openings, said openings having a diameter ranging from about eight millimeters to eighteen millimeters, the diameter of said fabric samples is greater than about two times the diameter of said openings; and a gap of at least about one millimeter gap exists between said first plate and said second plate;

protruding said fabric samples completely through said openings without piercing said fabric samples by translating said sample holder in a direction normal to the blunt end of at least one probe at a constant speed, wherein said openings are shaped in a fashion that allows said fabric samples to fold naturally providing a smooth transition for said fabric samples to transfer from a flat state to a bent and folded state during said protrusions, and allows contact to exist between said fabric samples and said openings' interior walls during said protrusions;

monitoring responses of said fabric samples to said protrusions with at least one sensor and a data logger for recording said response which includes measuring said force exerted on said at least one probe by said fabric samples as functions of displacement between said at least one probe and said fabric samples and measuring said force exerted on said at least one probe by said fabric samples as functions of time; and conducting an analysis selected from the following group consisting of relative comparison of the fabric handle of said fabric samples, quantitative measurement of the fabric handle of said fabric samples; comparison of the fabric handle of said fabric samples with the fabric handle of fabric materials not included in said array.

28. The method of claim 27, wherein the method is capable of screening at least four of said fabric samples simultaneously.

29. A method for screening fabric handle of an array of fabric samples, comprising:

placing an array of fabric samples having at least two fabric samples onto a sample holder having a plurality of openings having a diameter ranging from about eight millimeters to eighteen millimeters, and wherein said fabric samples do not overlap each other and are individually confined in specific locations that are aligned with said openings, each of said specific locations includes and extends beyond a region defined by diameter of said openings, and the diameter of said fabric samples is greater than about two times the diameter of said openings;

protruding said fabric samples completely through said openings without piercing said fabric samples by translating blunt end of at least one probe in a direction normal to said array at a constant speed, wherein said openings are shaped in a fashion that allows said fabric samples to fold naturally providing a smooth transition for said fabric samples to transfer from a flat state to a bent and folded state during said protrusions, and allows contact to exist between said fabric samples and said openings' interior walls during said protrusions; and monitoring responses of said fabric samples to said protrusions with at least one sensor and a data logger for recording said response which includes measuring said force exerted on said at least one probe by said fabric samples as functions of displacement between said at least one probe and said fabric samples and measuring said force exerted on said at least one probe by said fabric samples as functions of time; and conducting an analysis selected from the following group consisting of relative comparison of the fabric handle of said fabric samples, quantitative measurement of the fabric handle of said fabric samples; comparison of the fabric handle of said fabric samples with the fabric handle of fabric materials not included in said array.

30. The method of claim 29, wherein average sample throughput is not more than about two minutes per said fabric sample.

31. A method for screening fabric handle of an array of fabric samples, comprising:

providing an array of at least four fabric samples upon at least one substrate;

causing protrusions of each of said fabric samples through openings in said at least one substrate wherein said protrusions are caused by contacting a probe with said fabric samples using an automated system that moves said probe, said fabric samples, or both relative to each other and wherein said protrusions are caused at a throughput rate no greater than about two minutes per sample; and monitoring a response of each of said fabric samples to said protrusions for assisting in measuring relative fabric handle for each of said fabric samples;

wherein said array of fabric samples are placed into a sample holder having a first plate having a plurality of through-holes and a second plate having a plurality of openings that are aligned forming tunnels within said sample holder wherein said fabric samples are individually confined in specific locations that are between said first plate and said second plate, and each of said specific locations includes and extends beyond a region defined by diameter of said openings.

32. The method of claim 31, wherein a gap of at least about one millimeter gap exists between said first plate and said second plate.

33. The method of claim 31, wherein the method is capable of screening at least two of said fabric samples simultaneously.

34. The method of claim 31, wherein the method is capable screening at least twenty-four of said fabric samples simultaneously.

35. The method of claim 31, wherein average sample throughput is not more than about 20 seconds per said fabric sample.

36. The method of claim 31, wherein said array contain at least two different fabric materials.

37. The method of claim 31, wherein said fabric samples comprise of at least one material selected from the group consisting of woven materials, non-woven materials, knit materials, pile materials, blend materials, composite materials, and a combination thereof.

38. The method of claim 31, wherein at least one of said fabric samples has been subject to textile treatment selected from the group consisting of acrylic coating, airo finishing, bleaching, resin treatment, sanding, scenting, shearing, silver coating, wax coating, stonewashing, bonding, enzyme washing, flocking, glazing, mercerizing, milling, fulling, color treatment, texture treatment, bacterial resistant treatment, soil resistant treatment, oil repellent treatment, flame resistant treatment, pill resistant treatment, water resistant treatment, mildew resistant treatment, water repellant treatment, wrinkle resistant treatment, ultra violet resistant treatment, and a combination thereof.

39. The method of claim 31, wherein at least one of said fabric samples has been treated with an additive selected from the group consisting of binders, surfactants, fillers, reinforcements, flame retardants, colorants, environmental protectants, performance modifiers, control agents, plasticizers, cosolvents, accelerators, and a combination thereof.

40. The method of claim 31, wherein said protrusions are completed without piercing said fabric samples.

41. The method of claim 31, wherein said openings are shaped in a fashion that allows said fabric samples to fold naturally providing a smooth transition for said fabric samples to transfer from a flat state to a bent and folded state during said protrusions, and allows contact to exist between said fabric samples and said openings' interior walls during said protrusions.

42. The method of claim 31, wherein each of said openings is funnel-shaped having its top diameter that is about twice of its bottom diameter and its sloped section is about at least equal to height of its straight section.

43. The method of claim 31, wherein said monitoring response of said fabric samples to said protrusions are performed by at least one sensor and a data logger for recording said response.

44. The method of claim 31, further comprised of conducting an analysis selected from the group consisting of relative comparison of the fabric handle of said fabric samples, quantitative measurement of the fabric handle of said fabric samples, and comparison of the fabric handle of said fabric samples with the fabric handle of fabric materials not included in said array.

45. The method of claim 31, wherein monitoring said response of said fabric samples to said protrusions includes measuring said force exerted on said at least one probe by said fabric samples as functions of displacement between said at least one probe and said fabric samples.

46. The method of claim 31, wherein monitoring said response of said fabric samples to said protrusions includes measuring said force exerted on said at least one probe by said fabric samples as functions of time.

47. The method of claim 31, wherein said protrusions are caused by having a blunt end of said at least one probe translating in a direction normal to said array.

* * * * *

UNITED STATES PATENT AND TRADEMARK OFFICE
CERTIFICATE OF CORRECTION

PATENT NO. : 6,860,148 B2
DATED : March 1, 2005
INVENTOR(S) : Kossuth et al.

It is certified that error appears in the above-identified patent and that said Letters Patent is hereby corrected as shown below:

Column 19,
Line 47, delete "a" between "contacting" and "said"
Line 61, insert -- of -- before "screening"

Column 23,
Line 14, delete "capable screening" and insert -- capable of screening --

Signed and Sealed this

Thirty-first Day of May, 2005

JON W. DUDAS
*Director of the United States Patent and Trademark Office*